United States Patent
Macfie et al.

(10) Patent No.: US 9,201,038 B2
(45) Date of Patent: Dec. 1, 2015

(54) SYSTEM AND METHODS TO ACCOUNT FOR INTERFERENTS IN A GLUCOSE BIOSENSOR

(75) Inventors: Gavin Macfie, Inverness (GB); Zuifang Liu, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 529 days.

(21) Appl. No.: 13/556,923

(22) Filed: Jul. 24, 2012

(65) Prior Publication Data

US 2014/0027312 A1    Jan. 30, 2014

(51) Int. Cl.
G01N 27/327    (2006.01)
(52) U.S. Cl.
CPC .................... G01N 27/3274 (2013.01)
(58) Field of Classification Search
CPC ..................... G01N 27/327–27/3274
USPC ....................... 204/403.01–403.15
See application file for complete search history.

(56) References Cited

U.S. PATENT DOCUMENTS

| 6,413,398 | B1 | 7/2002 | Gerhardt et al. |
| 2004/0260511 | A1 | 12/2004 | Burke et al. |
| 2008/0000780 | A1 | 1/2008 | Tonks |
| 2010/0258451 | A1 | 10/2010 | Adlassnig |

FOREIGN PATENT DOCUMENTS

| EP | 0396788 A1 | 11/1990 |
| EP | 2138841 A2 | 12/2009 |
| GB | 2296333 A | 6/1996 |
| WO | WO 03/097860 A1 * | 11/2003 |
| WO | WO 2012/084194 A1 | 6/2012 |

OTHER PUBLICATIONS 2.3.3 Square-Wave Voltammetry from Analytical Electrochemistry, Joseph Wang, 1994, Wiley-VCH, p. 38-41.*
International Application No. PCT/GB2013/051957, International Search Report dated Oct. 21, 2013, 11 pages.

\* cited by examiner

*Primary Examiner* — J. Christopher Ball

(57) ABSTRACT

Various embodiments that allow for improved accuracy in the measurement of glucose with a glucose meter and a biosensor, principally, by using pulsed signal inputs to the biosensor and selecting at least one specific pulsed output from the biosensor to determine a glucose concentration that is less affected by interfering chemical substances that might be present in the fluid sample.

23 Claims, 17 Drawing Sheets

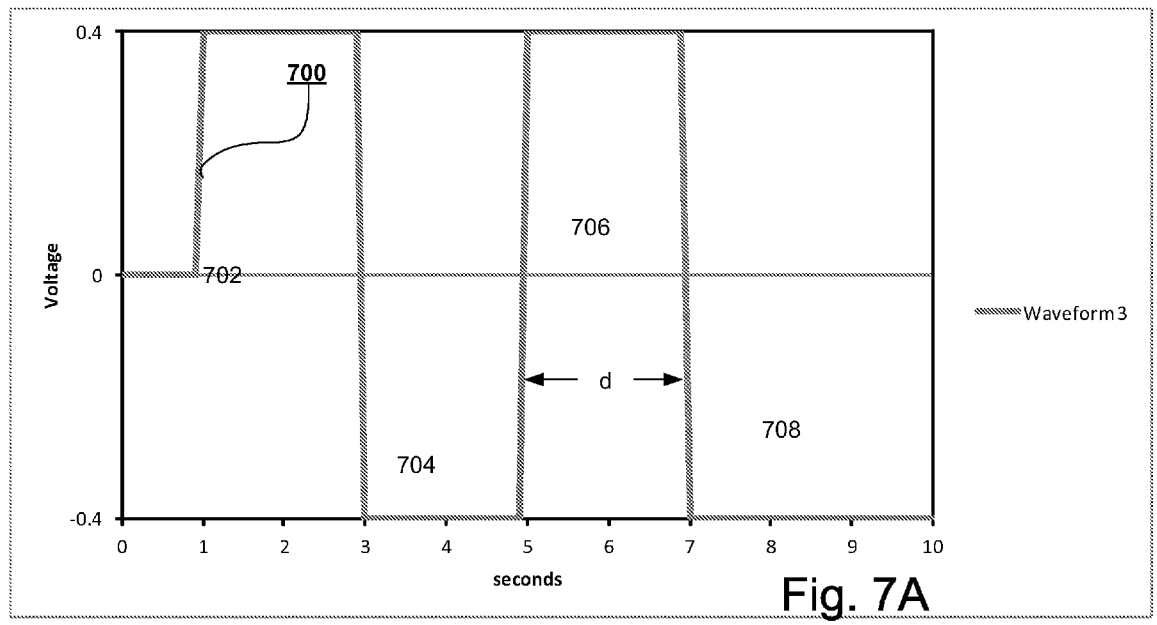
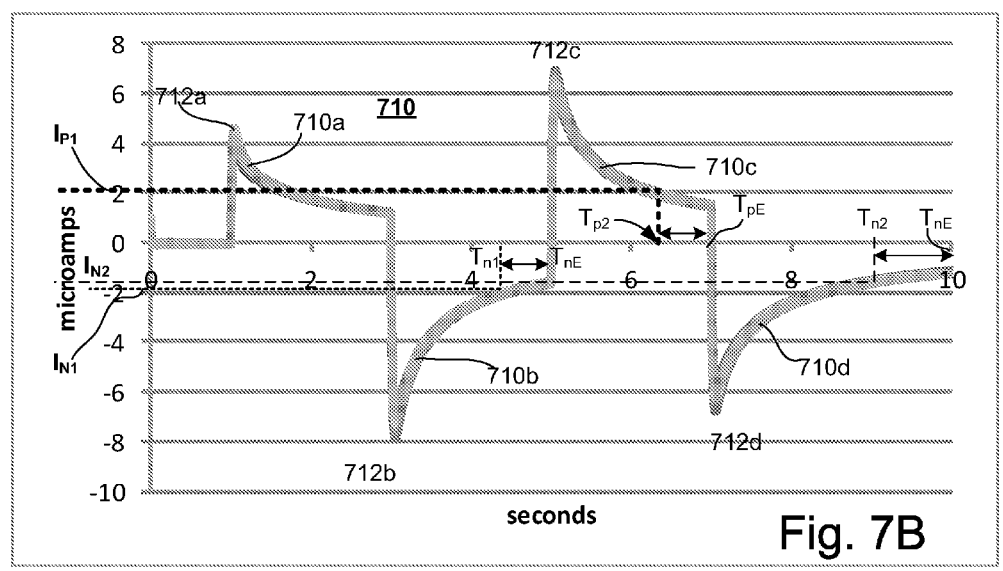

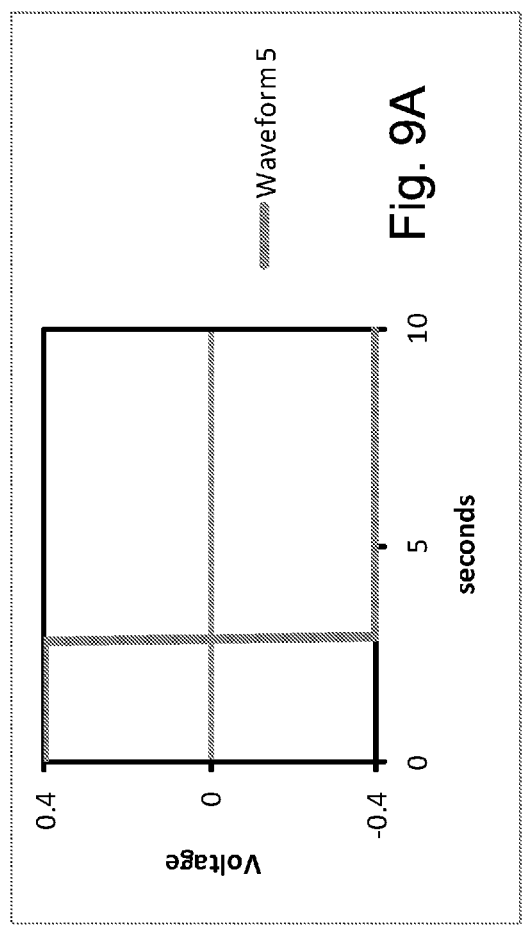
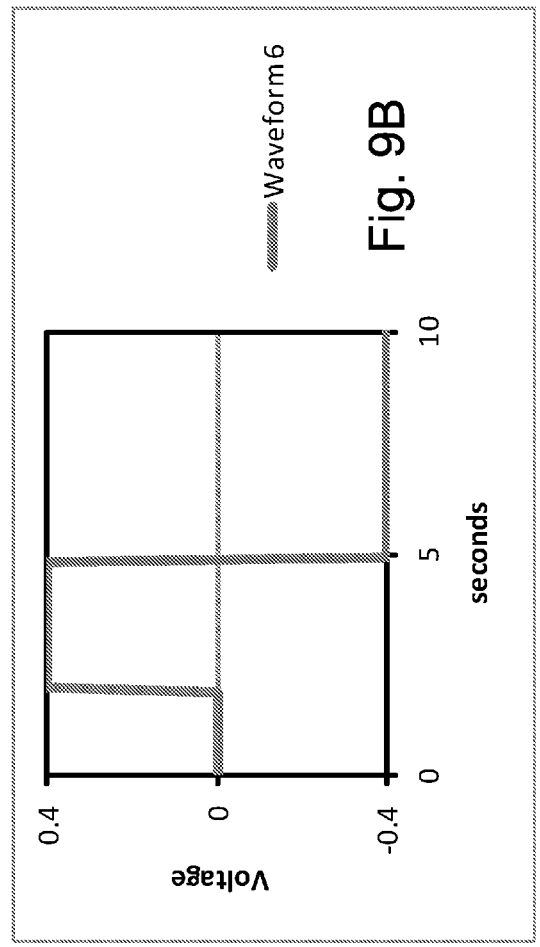

SYSTEM AND METHODS TO ACCOUNT FOR INTERFERENTS IN A GLUCOSE BIOSENSOR

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on a physical transformation (i.e., the selective oxidation) of glucose by the enzyme glucose oxidase (GO). The reactions that can occur in a glucose biosensor are summarized below in Equations 1 and 2.

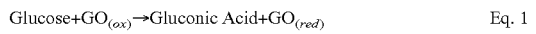

Eq. 1

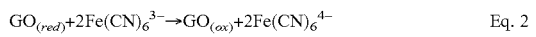

Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the chemical reaction in Equation 1, the oxidized enzyme $GO_{(ox)}$ is transformed to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation or transformation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Because it can be very important to know the concentration of glucose in blood, particularly in people with diabetes, glucose meters in the form of episodic glucose meter or continuous glucose monitors have been developed using the principles set forth above to enable the average person to sample and test their blood for determining their glucose concentration at any given time. The glucose current generated is detected by the glucose meter and converted into a glucose concentration reading using an algorithm that relates the test current to a glucose concentration via a simple mathematical formula. In a popular form of the glucose meter, the glucose meters work in conjunction with a biosensor (which is disposable) that may include a sample-receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample-receiving chamber, thus starting the chemical reaction set forth above.

For glucose measurements made using electrochemical sensors, such measurements are susceptible to measurement errors arising from the presence of endogenous and exogenous substances in the blood sample (interferent compounds). Such interferent compounds give rise to a measurement error through two mechanisms. Firstly, the interferent compound may be directly oxidised at the electrode surface, giving rise to an error current. Secondly, the interferent compound may react with the mediator, giving rise to an error current.

SUMMARY OF THE DISCLOSURE

Applicants have discovered various embodiments of a technique to allow for improved accuracy in the measurement of analyte with an analyte meter and a biosensor, principally, by using pulsed signal inputs to the biosensor and selecting at least one specific output from the biosensor to determine an analyte concentration that is less affected by interfering chemical substances that might be present in the fluid sample. In particular, applicants have discovered that whenever a positive potential is applied to an electrochemical biosensor with a sample, the sample generates a current response through three mechanisms: (1) an analyte signal is generated through oxidation of a suitable reduced acceptor (e.g., ferrocyanide) resulting from the enzyme reaction; (2) an interferent signal is generated through the oxidation of the reduced acceptor resulting from the reduction of the acceptor by interferent compounds in the blood; and (3) an interferent signal is generated through the direct oxidation of interferent compounds in the blood. On the other hand, where a negative potential is applied to the sample following a positive potential, the sample generates a current response through two mechanisms: (1) the oxidized form of the reduced acceptor (e.g., ferricyanide) is generated during the positive pulse is reduced back to its original form (e.g., to ferrocyanide) during the negative pulse; and (2) any electrochemically reversible interferent compounds are reduced back to their initial form. Applicants note that any electrochemically irreversible interferent compounds will not be reduced back to their initial form and will therefore not be able to contribute any interferent signal to subsequent pulses. Interferent signals arising from direct oxidation of electrochemically irreversible interferent compounds in the blood will thus be reduced. Hence, the current responses measured during both the initial negative pulse and the subsequent positive pulse will have a reduced contribution from electrochemically irreversible interferent compounds. It follows from the discussion above that in the case of a 'pulsed' waveform which contains both positive and negative voltage pulses, an analyte determination made using the current response resulting from the application of either the initial or a subsequent negative pulse or an analyte determination made using the current response resulting from the application of a positive pulse applied subsequently to a negative pulse, the error current due to the presence of irreversibly electrochemically active interferent compounds in the blood sample, and hence the measurement error in the analyte determination, will be reduced in the case of the 'pulsed' waveform with respect to that in the case of an analyte determination made using the current response resulting from the application of a single, positive, voltage pulse.

Based on the above discoveries, applicants have devised, in one aspect, an analyte measurement system that includes a biosensor and an analyte meter. The biosensor has at least two electrodes with a reagent disposed proximate the at least two electrodes. The analyte meter includes a power supply and memory for storage of data and a microprocessor. The microprocessor is coupled to the power supply and memory, and the biosensor. The microprocessor is configured to determine an analyte concentration in a physiological sample by: application of positive and negative electrical pulses to the at least two electrodes in sequence with a plurality of positive electrical pulses, in which a voltage of at least one positive electrical pulse is at a generally constant magnitude during at least one discrete interval, and a voltage of at least one negative electrical pulse is at a generally constant magnitude during at least one discrete interval; obtain at least one current output over a predetermined time period from the at least two electrodes for each of the plurality of electrical pulses other than the first electrical pulse; and calculate an analyte concentration based on the at least one current output.

In a second aspect, an analyte measurement system that includes a biosensor and an analyte meter is provided. The biosensor has at least two electrodes with a reagent disposed proximate the at least two electrodes. The analyte meter includes a power supply and memory for storage of data and a microprocessor. The microprocessor is coupled to the power supply and memory, and the biosensor. The microprocessor is configured to determine an analyte concentration in a physiological sample by: application of positive and negative electrical pulses to the at least two electrodes in sequence with a number of electrical pulses in the sequence, in which the electrical pulses are applied over discrete intervals and during each interval, a voltage of each of the positive electrical pulses is at a generally constant magnitude, and a voltage of at least one negative electrical pulse is at a generally constant magnitude; obtain at least a first current output from the at least two electrodes for each of a first predetermined time period due to application of at least one positive electrical pulse in the sequence other than the first positive pulse; obtain at least a second current output from the at least two electrodes for each of a second predetermined time period due to application of at least one negative electrical pulse in the sequence; and calculate an analyte concentration based on at least one of the first and second current outputs.

In a third aspect, a method to determine analyte concentration in a physiological sample with analyte meter and biosensor is provided. The meter has a microprocessor coupled to a power supply and memory. The biosensor has a reagent disposed on at least two electrodes. The method can be achieved by: depositing a physiological fluid sample on the reagent proximate the at least two electrodes of the biosensor; applying a plurality of positive and negative electrical pulses to the at least two electrodes in sequence with a plurality of positive electrical pulses with a positive electrical pulse being first in the sequence and at least one positive electrical pulse being next to the last pulse in the sequence, the applying step includes: driving the plurality of positive electrical pulses over discrete time intervals and during each interval, a voltage of each of the positive electrical pulses is at a generally constant magnitude, and driving at least one negative electrical pulse over at least one discrete time interval and during the at least one discrete interval, a voltage of the at least one negative electrical pulse is at a generally constant magnitude; measuring a first current output over a first predetermined time duration from the at least two electrodes due to application of at least one negative electrical pulse in the sequence; measuring a second current output over a second predetermined time period from the at least two electrodes due to application of at least one negative electrical pulse in the sequence; determining an analyte concentration based on at least one of the first and second current outputs; and annunciating the analyte concentration from the determining step.

In each of the above aspects, each of the following features can be utilized alone or in combination with other features elucidated here. For example, the biosensor may include a substrate on which the at least two electrodes are disposed, in which the at least two electrodes may include three electrodes, of which one of the three includes a reference electrode and two of the three are working electrodes; the at least one current output may be a negative current output of the last electrical pulse; the microprocessor is configured to calculate the analyte concentration with an equation of the form:

$$G_N = \frac{(|I_N| - \text{Intercept})}{\text{Slope}}$$

where $I_N$ may be a negative current output from the last electrical pulse of the sequence;

Slope may be the value obtained from calibration testing of a batch of biosensors of which this particular biosensor comes from; and Intercept may be the value obtained from calibration testing of a batch of biosensors of which this particular biosensor comes from.

Alternatively, the microprocessor is configured to calculate the analyte concentration with an equation of the form:

$$G = \frac{(|I_E| - \text{Intercept})}{\text{Slope}}$$

where $I_E$ may be an average of the first current output $I_P$ and second current output $I_N$;

$I_P$ may be at least one current output or an average current output of the first output currents measured from each positive pulse other than the first positive pulse;

$I_N$ may be at least one current output or an average current output of the second output currents measured from each negative pulse in the sequence;

Slope may be the value obtained from calibration testing of a batch of biosensors of which this particular biosensor comes from; and Intercept may be the value obtained from calibration testing of a batch of biosensors of which this particular biosensor comes from.

Again, each of the following features may be utilized. For example, each of the first output currents and second output currents may be an output current measured at a predetermined time within each of the k number of pulses; each of the first output currents may be a summation of the positive output currents over a predetermined time duration during each pulse in the sequence of k pulses; each of the second output currents may be a summation of the negative output currents over a predetermined time duration during each pulse of the sequence of k pulses and k may be any whole number of at least 2; the microprocessor is configured to calculate the analyte concentration with an equation of the form:

$$G_P = \frac{(|I_P| - \text{Intercept})}{\text{Slope}}$$

where $I_P$ may be an average of output currents measured from positive electrical pulses of the sequence other than the first positive electrical pulse in the sequence;

Slope may be the value obtained from calibration testing of a batch of biosensors of which this particular biosensor comes from; and Intercept may be the value obtained from calibration testing of a batch of biosensors of which this particular biosensor comes from.

Additionally, each of the following features may be utilized alone or in combination with other features: the analyte concentration may be an average of the sum of the analyte concentrations $G_P$ and $G_N$; the first current may be an average of current outputs over the first predetermined time period within each pulse of the sequence of k pulses; the first current may be a summation of current outputs over the first predetermined time period within each pulse of the sequence of k pulses; the second current may be an average of current outputs over the second predetermined time period within each pulse of the sequence of k pulses; the second current may be a summation of current outputs over the second predetermined time period within each pulse of the sequence of k pulses; each of the first and second predetermined time periods may be about the same duration of time; the first predetermined time period may be about 200 milliseconds and the second predetermined time period may be about 200 milliseconds; the sequence of electrical pulses may be about 4 electrical pulses; the sequence of electrical pulses may be about 6 electrical pulses; the sequence of electrical pulses may be about 10 electrical pulses; the magnitude of the positive electrical pulse may be about 400 millivolts and the magnitude of the negative electrical pulse may be about negative 400 millivolts; the duration of the positive electrical pulse may be about any duration from about 0.5 seconds to about 5 seconds; the duration of the negative electrical pulse may be about any duration from about 0.5 seconds to about 5 seconds.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 7A illustrates a graph of four electrical pulses similar to the pulses in FIG. 5A but with longer duration being driven into the biosensor of the preferred embodiments.

FIG. 7B illustrates a graph of four corresponding output pulses from the biosensor that are due to the input pulses of FIG. 7A.

FIGS. 9A-9D illustrate other pulsing wave forms that can be used with the techniques disclosed herein.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1:
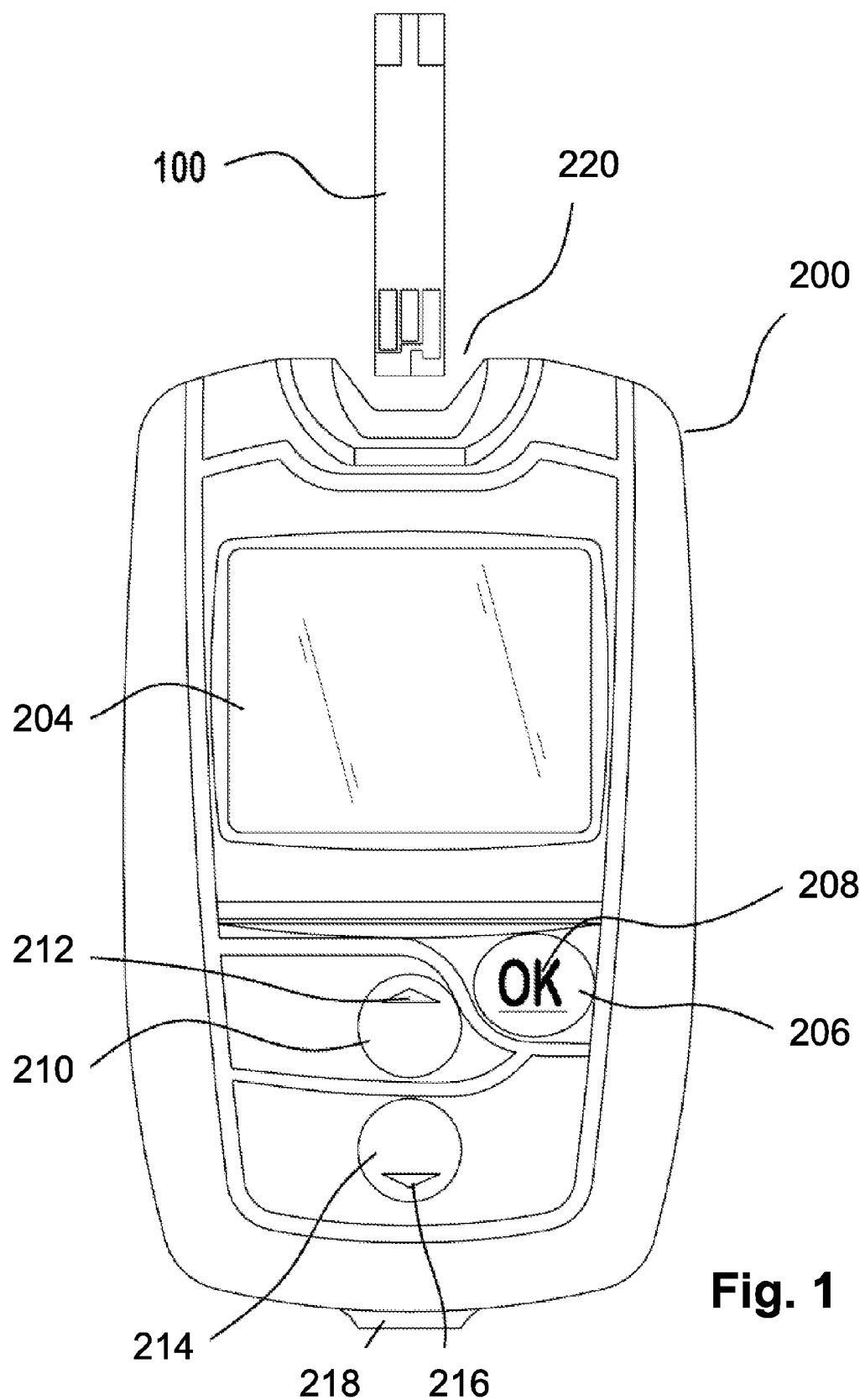
FIG. 1 illustrates an analyte measurement system.

FIG. 1 illustrates an analyte meter 200, for testing analyte levels in the blood of an individual with a biosensor produced by the methods and techniques illustrated and described herein. Analyte meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Analyte meter 200 can also include a display 204 that can be used to report measured analyte levels, and to facilitate entry of lifestyle related information.

Analyte meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Analyte meter 200 can be turned on by inserting a biosensor 100 into a strip port connector 220, by pressing and briefly holding first user interface input 206, or by the detection of data traffic across a data port 218. Analyte meter 200 can be switched off by removing biosensor 100, pressing and briefly holding first user interface input 206, navigating to and selecting a meter off option from a main menu screen, or by not pressing any buttons for a predetermined time. Display 104 can optionally include a backlight.

In one embodiment, analyte meter 200 can be configured to not receive a calibration input for example, from any external source, when switching from a first biosensor batch to a second biosensor batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the biosensor batches have a substantially uniform calibration characteristic. The calibration input can be a set of values ascribed to a particular biosensor batch. For example, the calibration input can include a batch slope and a batch intercept value for a particular biosensor batch. The calibrations input, such as batch slope and intercept values, may be preset within the meter as will be described below.

Figure 2:
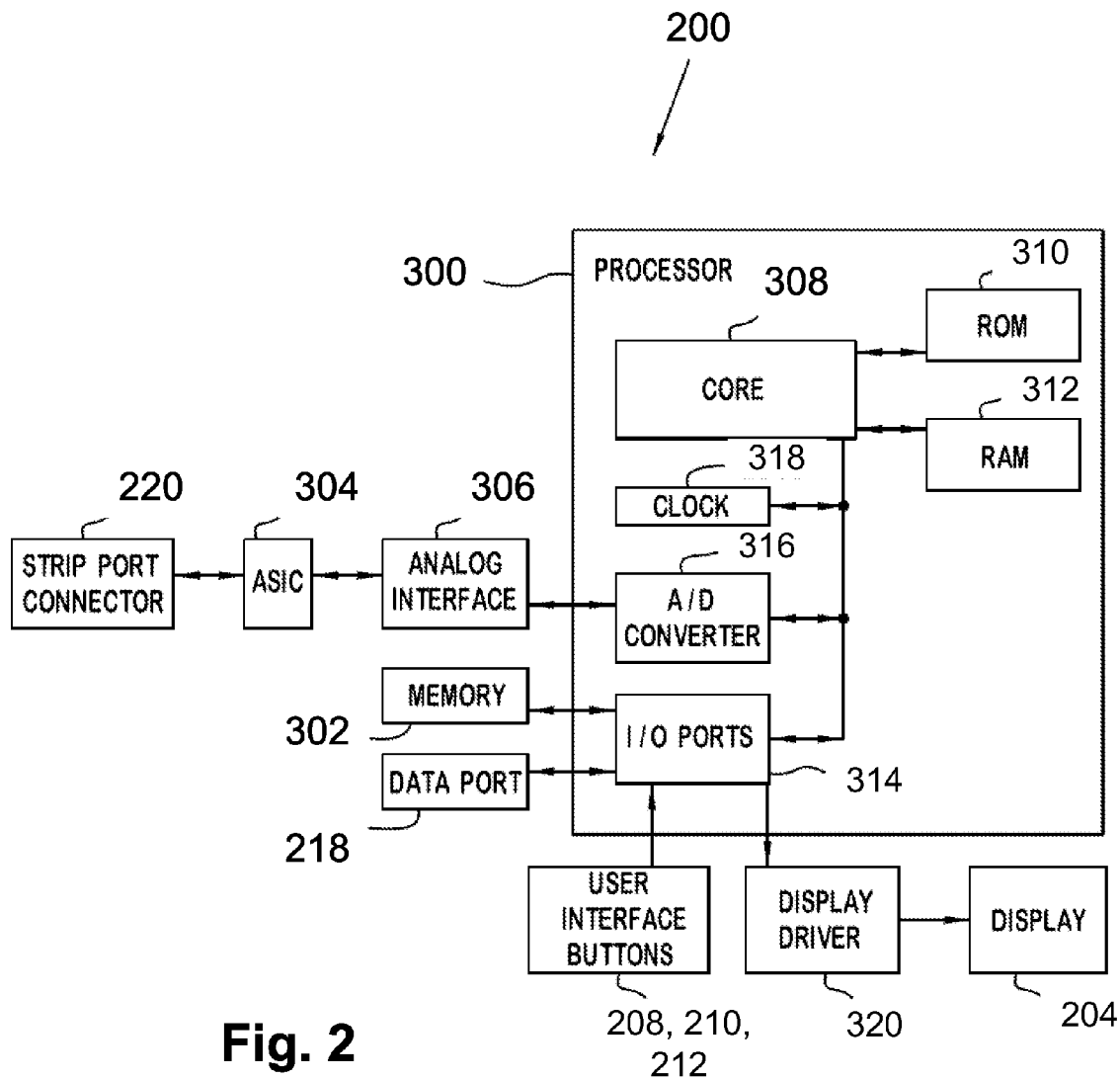
FIG. 2 illustrates in simplified schematic form the components of the meter 200.

Referring to FIG. 2, an exemplary internal layout of analyte meter 200 is shown. Analyte meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of analyte meter 200. This pre-loaded calibration information can be accessed and used by processor 300 upon receiving a suitable signal (such as current) from the strip via strip port connector 220 so as to calculate a corresponding analyte level (such as blood analyte concentration) using the signal and the calibration information without receiving calibration input from any external source.

In embodiments described and illustrated herein, analyte meter 200 may include an Application Specific Integrated Circuit (ASIC) 304, so as to provide electronic circuitry used in measurements of analyte level in blood that has been applied to a biosensor 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit.

Figure 3A:
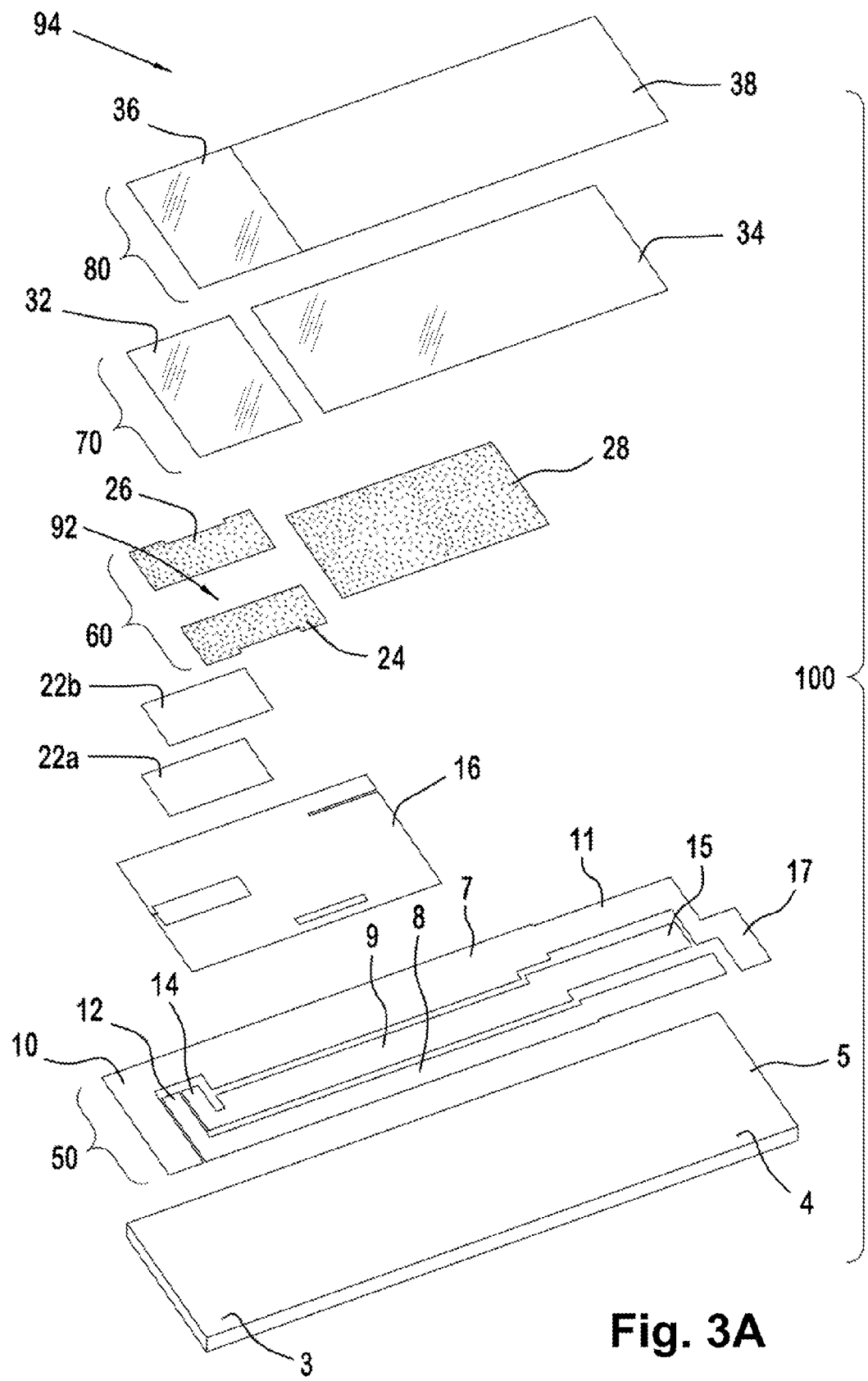
FIG. 3A illustrates the biosensor 100 of the system of FIG. 1.

FIG. 3A is an exemplary exploded perspective view of a biosensor 100, which may include seven layers disposed on a substrate 5. The seven layers disposed on substrate 5 can be a conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Biosensor 100 may be manufactured in a series of steps where the conductive layer 50, insulation layer 16, reagent layers 22, adhesive layer 60 are sequentially deposited on substrate 5 using, for example, a screen-printing process. Hydrophilic layer 70 and top layer 80 can be disposed from a roll stock and laminated onto substrate 5 as either an integrated laminate or as separate layers. Biosensor 100 has a distal portion 3 and a proximal portion 4 as shown in FIG. 3A.

Biosensor 100 may include a sample-receiving chamber 92 through which a blood sample may be drawn. Sample-receiving chamber 92 can include an inlet at a proximal end and an outlet at the side edges of biosensor 100, as illustrated in FIG. 3A. A blood sample 94 can be applied to the inlet to fill a sample-receiving chamber 92 so that analyte can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A.

For biosensor 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of analyte. Conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

Figure 3B:
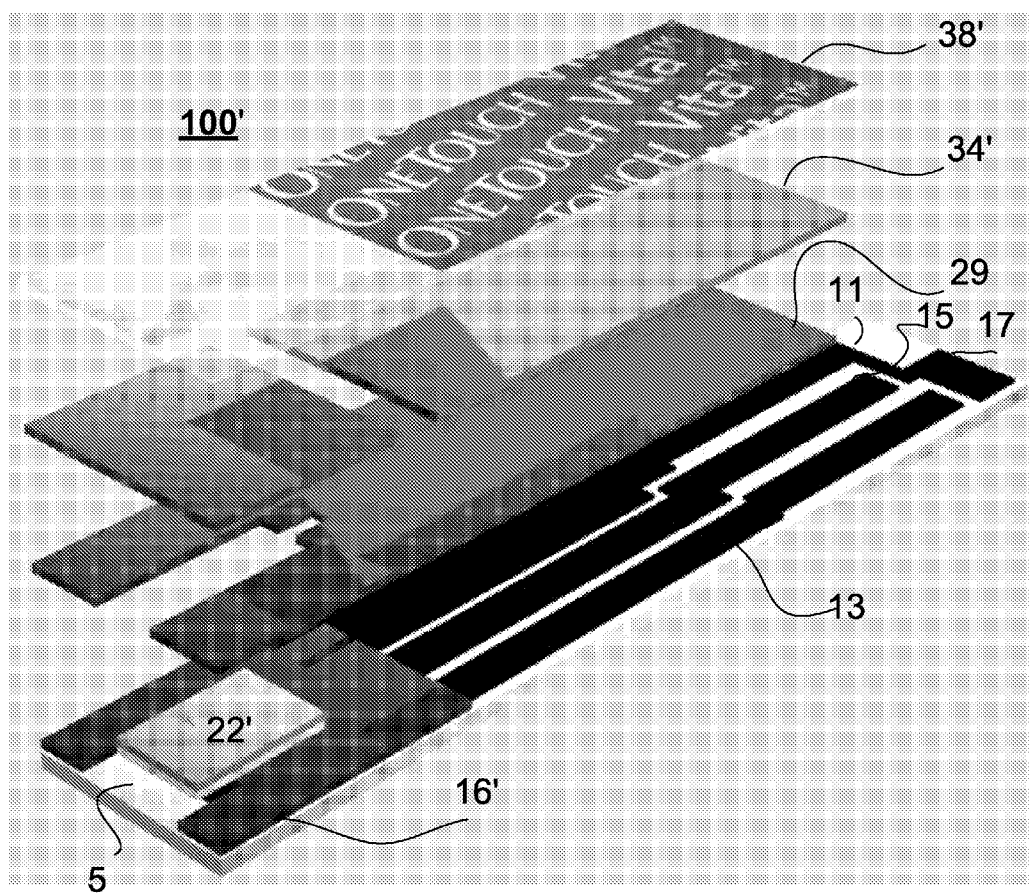
FIG. 3B illustrates an alternate biosensor 100' for the system of FIG. 1.

For biosensor 100, as illustrated in FIG. 3A, conductive layer 50 may include a reference electrode 10, a first working electrode 12, a second working electrode 14, a first contact pad 13, a second contact pad 15, a reference contact pad 11, a first working electrode track 8, a second working electrode track 9, a reference electrode track 7, and a strip detection bar 17. The conductive layer may be formed from carbon ink. First contact pad 14, second contact pad 15, and reference contact pad 11 may be adapted to electrically connect to an analyte meter. First working electrode track 8 provides an electrically continuous pathway from first working electrode 12 to first contact pad 14. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. An analyte meter can detect that biosensor 100 has been properly inserted by measuring a continuity between reference contact pad 11 and strip detection bar 17, as illustrated in FIG. 3A. An alternate version of the biosensor 100 is shown in FIG. 3B as biosensor 100'. In this version, the top layer 38', hydrophilic film layer 34' and spacer 29 have been combined together to form an integrated assembly for mounting to the substrate 5 with reagent layer 22' disposed proximate insulation layer 16'.

Figure 4A:
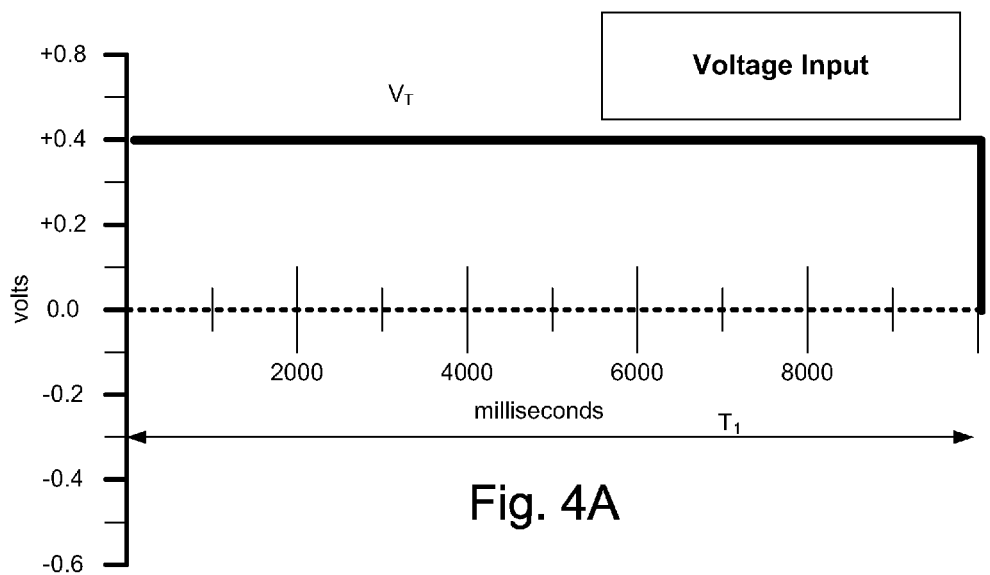
FIG. 4A illustrates a graph of time over applied potential of a known system.

FIG. 4A is an exemplary chart of a known analyte measurement technique to measure an analyte such as, for example, glucose with a suitable analyte meter such as for example, a glucose meter and a suitable biosensor such as, for example, a glucose test strip. In this exemplary system, a test voltage applied to biosensor 100. Before a fluid sample is applied to biosensor 100, analyte meter 200 is in a fluid detection mode in which a test voltage $V_{T1}$ of about 400 millivolts is applied between second working electrode 14 and reference electrode 10. A second test voltage $V_{T2}$ of about 400 millivolts is preferably applied simultaneously between first working electrode 12 and reference electrode 10. Alternatively, the second test voltage may also be applied contemporaneously such that a time interval of the application of the first test voltage overlaps with a time interval in the application of the second test voltage. The analyte meter may be in a fluid detection mode during fluid detection time interval prior to the detection of physiological fluid. In the fluid detection mode, analyte meter 200 determines when a fluid is applied to biosensor 100 such that the fluid wets second working electrode 14 and reference electrode 10. Once analyte meter 200 recognizes that the physiological fluid has been applied because of, for example, a sufficient increase in the measured test current at second working electrode 14, analyte meter 200 assigns a zero second marker at this so-called starting time as "0" and starts the test time interval $T_1$. Upon the completion of the test time interval $T_1$, the test voltage is removed. For simplicity, FIG. 4A only shows the first test voltage $V_{T1}$ applied to biosensor 100.

Figure 4B:
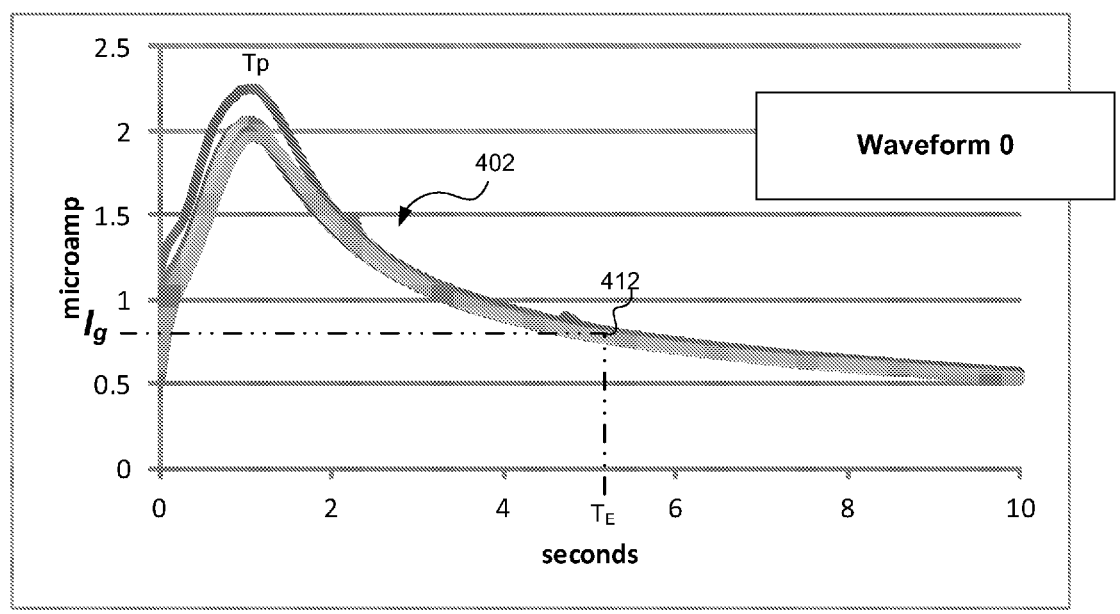
FIG. 4B illustrates a graph of time over output current from the biosensor of the known system.

Hereafter, a description of how glucose concentration is determined from the known current output transients (i.e., the measured electrical current response in microamperes as a function of time in FIG. 4B) that are measured when the test voltages of FIG. 4A are applied to the known biosensors 100.

In FIG. 4A, the test voltage applied to biosensor 100 is generally from about +100 millivolts to about +600 millivolts. In one embodiment in which the electrodes include carbon ink and the mediator is ferricyanide, and the analyte in question is glucose, the test voltage is about +400 millivolts. Other analytes, mediator and electrode material combinations will require different test voltages. The duration of the test voltage 402 is generally from about 2 to about 4 seconds after a reaction period and is typically about 3 seconds after a reaction period. Typically, time $T_1$ is measured relative to time a time point when the sample is detected on the biosensor's electrodes. As the voltage $V_{T1}$ is maintained in FIG. 4A for the duration of T1, the current transient 402 for the first working electrode is generated starting at zero time (and likewise the current transient for additional electrodes can also be generated with respect to the zero time). The current transient 402 builds up to a maximum proximate peak time Tp at which time, the current slowly drops off until approximately 5 seconds after zero time. At the point 412, the current value "Ig" for a working electrode is measured. Because the biosensor includes more than one working electrodes, a plurality of current transients besides current transient 402 can be provided by the biosensor. Where there are more than one working electrodes, the current outputs Ig at sampling time Te is added together to derive the output current that can be used to determine glucose concentration. It is noted that in one embodiment, the time Te is selected to be a single time point (or a range of time points) at a certain interval from a peak current output at time Tp. Alternatively, the time Te may be a fixed time point from the start time 0 of the test sequence. In yet another alternative, the time Te can be a time point selected from a table correlated to at least one physical characteristic of the sample. Details of this variable test time are shown and described in U.S. Provisional Patent Application Ser. No. 61/581,087 filed Dec. 29, 2011; 61/581,089 filed Dec. 29, 2011; 61/581,099 filed Dec. 29, 2011; and 61/581,100 filed Dec. 29, 2011, and which applications are hereby incorporated by reference into this application.

From knowledge of the calibration code offset and slope for the particular biosensor 100, the glucose concentration can be calculated. "Intercept" and "Slope" are the values obtained by measuring calibration data from a batch of test strips. Typically around 1500 strips are selected at random from the lot or batch. Body fluid from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current). A graph of measured glucose concentration is plotted against actual glucose concentration (or measured current versus YSI current), and a formula y=mx+c least squares fitted to the graph to give a value for batch slope m and batch intercept c for the remaining strips from the lot or batch.

As an example of an analyte calculation (e.g., glucose) for biosensor 100 (FIG. 3A), it is assumed in FIG. 4B that the sampled current value at 412 for the first working electrode is 1600 microamps whereas the current value at 412 for the second working electrode is 1400 microamps and for the calibration code of the biosensor the Intercept is 500 microamps and the Slope is 18 microamps/mg/dL. Glucose concentration G can be thereafter be determined from Equation 3 as follow:

$$G = [(Ig) - \text{Intercept}]/\text{Slope} \qquad \text{Eq. 3}$$

Where

Ig is the current measured from the electrode (FIG. 4B) or a sum of currents measured from the electrodes;

Slope is the value obtained from calibration testing of a batch of biosensors of which this particular biosensor comes from;

Intercept is the value obtained from calibration testing of a batch of biosensors of which this particular biosensor comes from.

From Eq. 3 G=[(1600+1400)−500]/18 and therefore, G=143.33 nanoamp~143 mg/dL.

It is noted that certain offsets may be provided to the current value of each working electrode to account for errors or delay time in the electrical circuit of the meter 200. Temperature compensation can also be utilized to ensure that the results are calibrated to a referential temperature such as for example room temperature of about 20 degrees Celsius.

Applicants have discovered that for blood samples that have "interferents," a glucose measurement can be obtained that is less affected by these interferents skewing (or in the art, "biasing") the glucose measurements away from its YSI laboratory's value. Applicants' approach is advantageous compared to known approaches for the reduction of error currents arising from oxidation of irreversibly electrochemically active interferent compounds. As used herein, the term "interferents" indicates substances that are the result of biochemical reactions in a biological system and not intrinsic to the physiological fluid sample, such as, for examples, uric acid, acetaminophen, dopamine, ascorbic acid, and the like.

In the known approach, the skewing effects of interferents may be reduced by directly measuring such currents at a dedicated electrode and using such a measured current to apply a correction to the final glucose measurement. The known approach requires the presence on the strip of an additional electrode. The presence of such an additional electrode requires a larger test chamber, which in turn requires a greater sample volume. Applicants' technique of voltage pulsing therefore reduces the volume requirement of the test chamber with respect to the approach of direct measurement and correction.

Figure 5A:
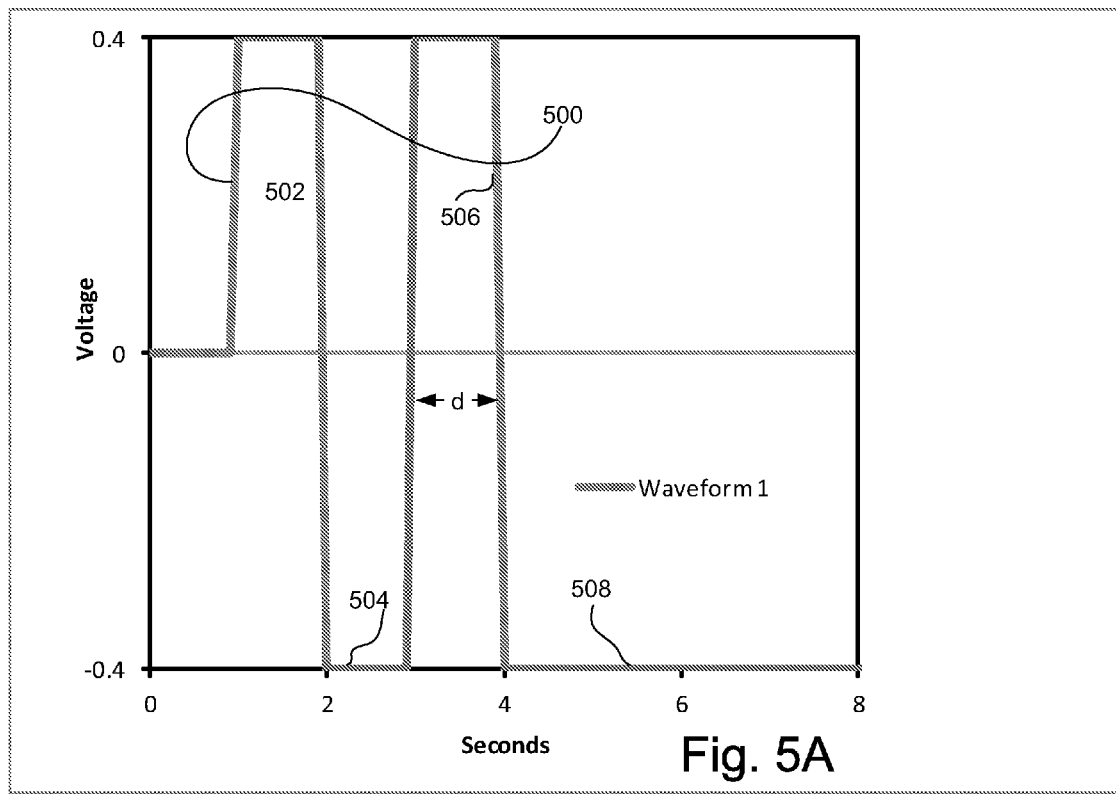
FIG. 5A illustrates a graph of four electrical pulses being driven into the biosensor of the preferred embodiments.

Specifically, applicants' new technique involves a determination of a glucose concentration in a physiological sample by application of a plurality of positive and negative electrical pulses to the at least two electrodes in a heretofore novel and unobvious manner discovered by applicants. As shown in FIG. 5A, the input voltage 500 is provided in the form of a sequence 500 of positive and negative pulses (502, 504, 506, and 508) at discrete time intervals. Each positive pulse (e.g., 502, 506) is applied over spaced apart intervals "d" and during each interval "d", a voltage of each of the positive electrical pulses is maintained at a generally constant magnitude. The interval can be from about 0.2 seconds to about 6 seconds. Each negative pulse (e.g., 504) is applied between the positive pulses at spaced apart intervals "d". During at least one discrete interval "d", a voltage of the at least one negative electrical pulse is at a generally constant magnitude. The negative pulse 504 can be maintained at a generally constant magnitude for an interval that can be from about 0.2 seconds to about 6 seconds. Each of the positive and negative pulses are in alternating sequence and that the first pulse can be of a first polarity and the second pulse can be of an opposite polarity. In the preferred embodiment, the first polarity may be a positive polarity and the positive and negative electrical pulses are applied to the at least two electrodes in sequence.

In applicants' approach, the plurality positive electrical pulses can include the first and next to last pulse (e.g., 502 and 506) in the sequence of pulses. There is at least one negative electrical pulse (e.g., pulse 504) being next to the last positive pulse in the sequence of pulses. The last pulse is preferably a negative pulse (e.g., 508). It is noted that the plurality of positive electrical pulses is applied over discrete spaced apart time-wise intervals at which a voltage of the positive electrical pulse is held at a generally constant magnitude during each interval. At least one negative electrical pulse, for example, negative pulse 504 or 508 (FIG. 5A), is applied over at least one discrete time interval at which a voltage of the negative electrical pulse is held at a generally constant magnitude during each interval.

Figure 5B:
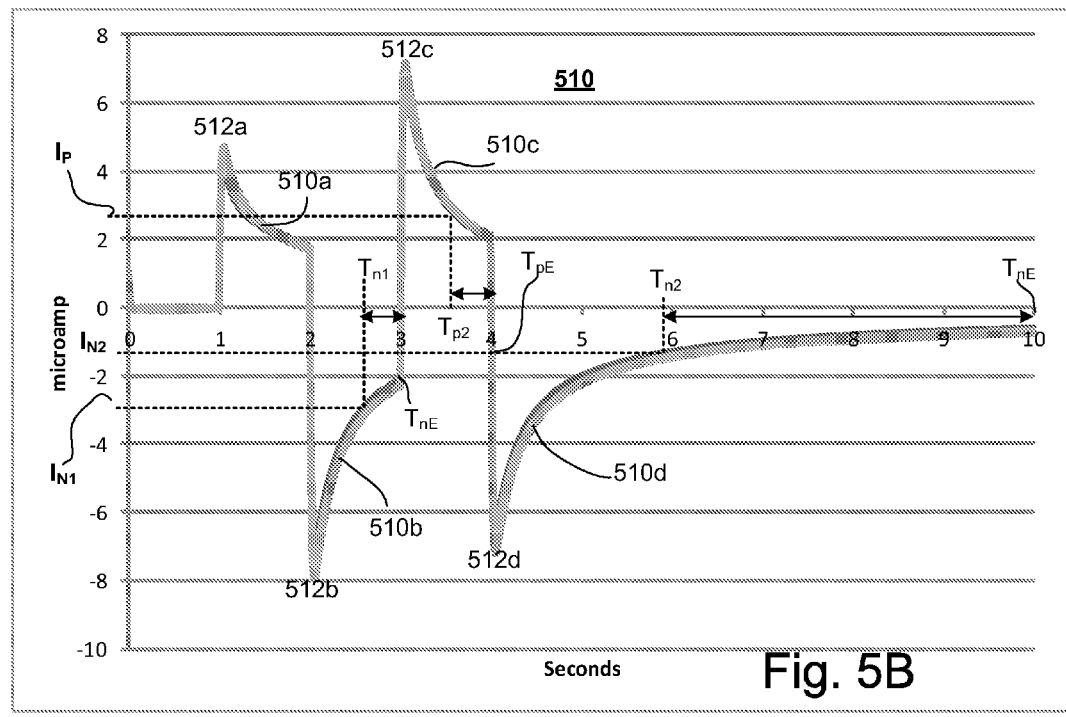
FIG. 5B illustrates a graph of four corresponding output pulses from the biosensor that are due to the input pulses of FIG. 5A.

With reference to exemplary FIG. 5B, each of the pulses applied (in FIG. 5A) to the biosensor will cause the analyte (in this case glucose) and reagent in the biosensor to provide output pulses 510 (in FIG. 5B showing an output transient waveform) with corresponding output pulse peaks (512a, 512b, 512c, and 512d) at the beginning of each input pulse (FIG. 5A). The output transient 510 is represented here as a current output over time and shown here as several decaying transients 510a, 510b, 510c, and 510d in which each of the transients is decaying from the respective peaks 512a, 512b, 512c, and 512d. In particular, the system obtains (e.g., by sampling or measuring a current transient) a current output $I_P$ from the at least two electrodes of the biosensor due to application of at least one electrical pulse other than the first pulse 502 in the sequence 500 of electrical pulses 502, 504, and 506. The current output $I_P$ can be measured at time Tp2, an average or summation of the output currents from the time point of Tp2 to the end of the decaying transient or the start of the next pulse (FIG. 5B). The system also obtains an output current $I_{N1}$ from the biosensor due to application of the first negative pulse 504 (FIG. 5A) at time $T_{N1}$, and another output current $I_{N2}$ due to application of the last electrical pulse (e.g., pulse 508) at time $T_{N2}$ in the sequence of pulses 502, 504, 506, and 508. A sum (or alternatively an average) of the output currents $I_{N1}$ and $I_{N2}$ can be designated as the current output $I_N$. Note that each of the output currents $I_{N1}$ and $I_{N2}$ can be measured at respective time $T_{N1}$ and $T_{N2}$. Alternatively, an average or summation of the output currents from each of respective time points of $T_{N1}$ and $T_{N2}$ to the end $T_{NE}$ of the decaying transient (or the start of the next pulse), whose duration is shown here as double-headed arrows.

The system may determine the glucose concentration with the first and second current outputs $I_P$ and $I_N$ in Equation 4 of the form:

$$G = \frac{(|I_E| - \text{Intercept})}{\text{Slope}} \qquad \text{Eq. 4}$$

where $I_E$ may be an average of the first current output $I_P$ and second current output $I_N$;

$I_P$ may be at least one current output or an average current output of the first output currents ($I_{P2}, I_{P3}, I_{P4}, I_{P5} \ldots I_{Pk}$ where k=total number of pulses) measured from each positive pulse other than the first positive pulse;

$I_N$ may be at least one current output or an average current output of the second output currents ($I_{N1}, I_{N2}, I_{N3} \ldots I_{Nk}$) measured from each negative pulse in the sequence;

Slope may be the value obtained from calibration testing of a batch of biosensors of which this particular biosensor comes from; and Intercept may be the value obtained from calibration testing of a batch of biosensors of which this particular biosensor comes from.

Alternatively, where the biosensor includes two working electrodes, the system may determine the glucose concentration with Equation 3 where each of the current output $I_P$ and current output $I_N$ can be obtained from each of the working electrodes. Where there is more than one current output, an average of the positive output currents $I_{P2}, I_{P3}, I_{P4}, I_{P5} \ldots I_{Pk}$ (where k=total number of pulses) from each of the working electrodes can be used along with an average of the negative output currents $I_{N1}, I_{N2}, I_{N3} \ldots I_{Nk}$ (where k=total number of pulses) from each of the working electrodes as the current I in Equation 3 above. To distinguish between the similar nomenclatures $I_P$ versus $I_{P2}$, $I_{P3}$, $I_{P4}$, $I_{P5}$ ... $I_{Pk}$, applicants have designated $I_P$ (or $I_N$) as "current output" and the series $I_{P2}$, $I_{P3}$, $I_{P4}$, $I_{P5}$ ... $I_{Pk}$ (or $I_{N1}$, $I_{N2}$, $I_{N3}$, $I_{N4}$ ... $I_{Nk}$) as "output currents."

Figure 11:
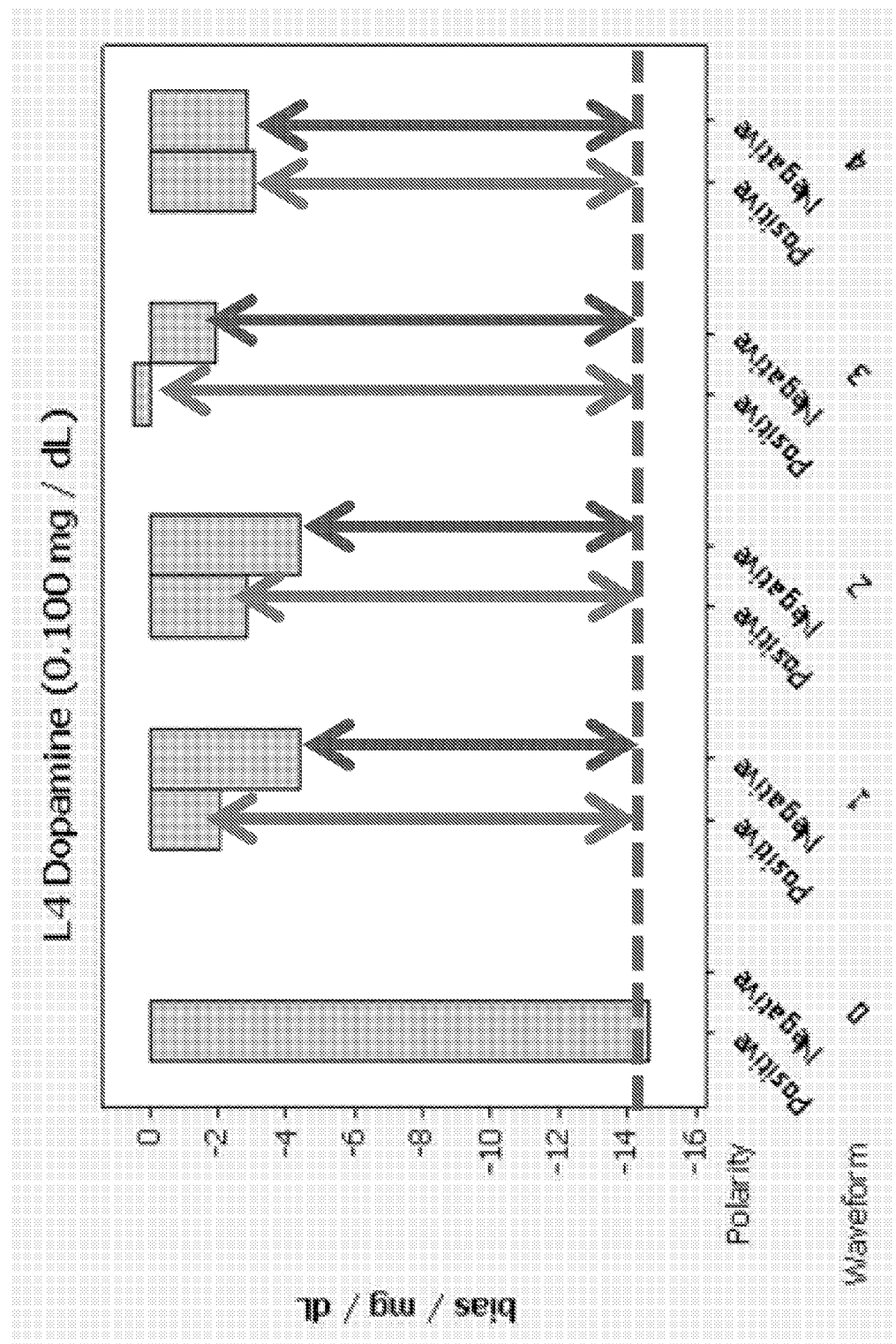
FIGS. 11-13 illustrate the reduction in bias when other interferents (e.g., dopamine, acetaminophen, or ascorbic acid) are added to the measurement samples while using the techniques of applicants' invention as compared to a known system and a referential datum.

Applicants have discovered that the error (or "bias") between a glucose measurement and a referential glucose measurement via the YSI laboratory equipment is reduced for particular interferent(s) when at least the last negative current is utilized in the glucose calculation. For example, as can be seen in FIG. 11, when the interferent is ascorbic acid and the Waveform is "1", the reduction in bias is greater in the negative pulse (at about 5 mg/dL) than the positive pulse (at about 7 mg/dL) as compared to the control in Waveform 0, (at about 10 mg/dL greater than referential YSI value). As applicants have discovered that bias is reduced in certain interferents via the use of the particularly selected negative pulse, it is also preferable that certain glucose concentration from the selected positive current(s) or selected negative current(s) be utilized separately when accounting for particular interferents and one of the two glucose readings (from respective positive and negative pulses) may be used as the glucose reading annunciated to the user. For example, the microprocessor can be configured to calculate the glucose concentration using the output of the selected negative pulse with Equation 5 of the form:

$$G_N = \frac{(|I_N| - \text{Intercept})}{\text{Slope}} \qquad \text{Eq. 5}$$

where
$I_N$ may include the second current output measured from the last electrical pulse of the sequence;
Slope may include the value obtained from calibration testing of a batch of biosensors of which this particular biosensor comes from; and
Intercept may include the value obtained from calibration testing of a batch of biosensors of which this particular biosensor comes from.

On the other hand, the microprocessor can also be configured to calculate the glucose concentration with Equation 6 of the form:

$$G_P = \frac{(|I_P| - \text{Intercept})}{\text{Slope}} \qquad \text{Eq. 6}$$

where
$I_P$ may include the first current output measured for a pulse other than the first positive pulse of the sequence of pulses;
Slope may include the value obtained from calibration testing of a batch of biosensors of which this particular biosensor comes from; and
Intercept may include the value obtained from calibration testing of a batch of biosensors of which this particular biosensor comes from.

Alternatively, both glucose measurements in Equations 5 and 6 (from respective positive and negative pulses) can also be averaged together to provide for a glucose concentration to the user.

Figure 6A:
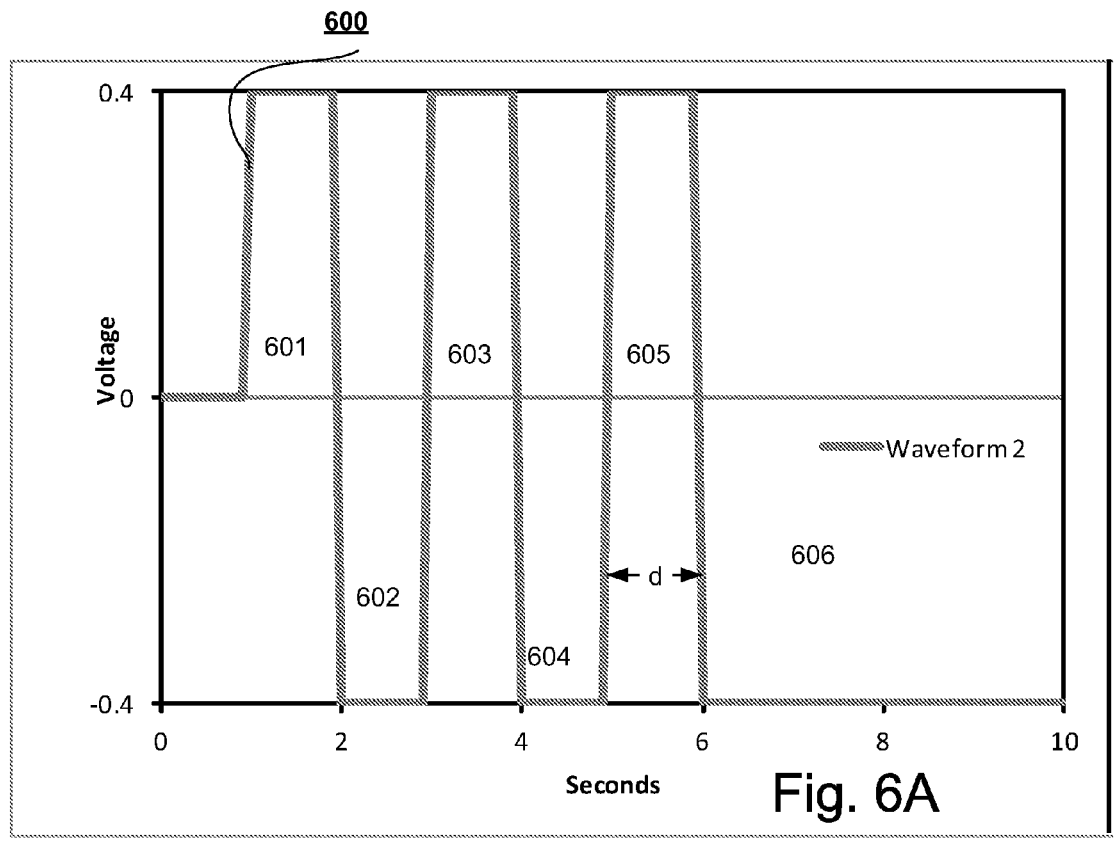
FIG. 6A illustrates a graph of six electrical pulses being driven into the biosensor of the preferred embodiments.
Figure 6B:
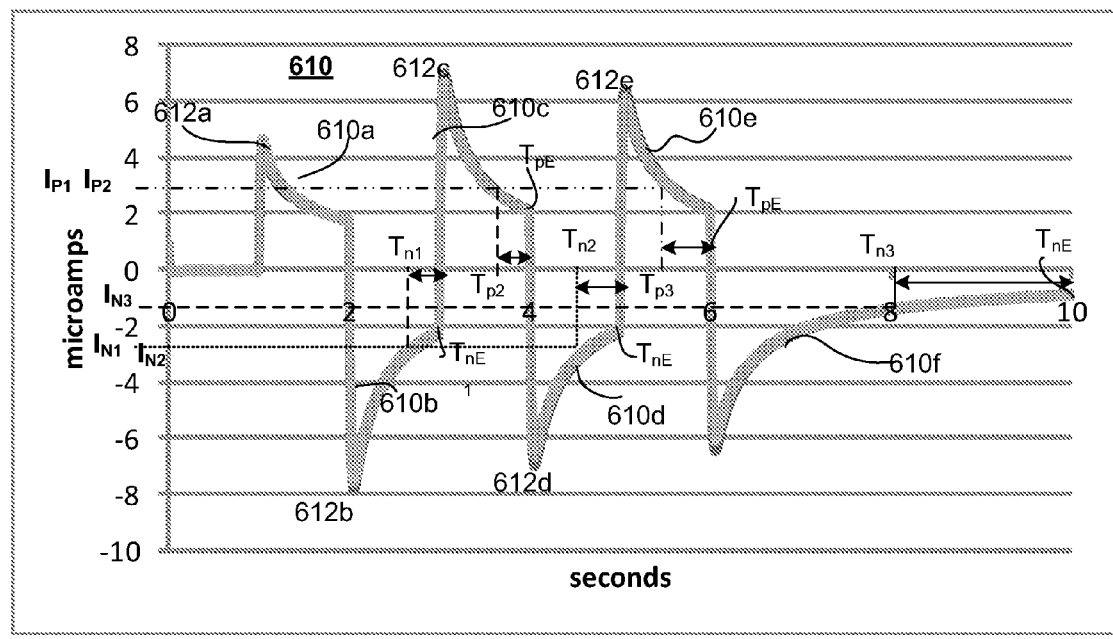
FIG. 6B illustrates a graph of six corresponding output pulses from the biosensor that are due to the input pulses of FIG. 5A that are due to the input pulses of FIG. 6A.

Another embodiment is also shown here in FIGS. 6A and 6B. In FIG. 6A, the system may generate a sequence of a "k" number of electrical pulses 600 that includes positive pulses 602, 606, 610 at spaced apart intervals with negative pulses 604 and 606 in between the spaced apart intervals of the positive electrical pulses. The sequence of electrical pulses 600 provided to the biosensor 100 generates the current transient 610 that includes peaks 612a, 612b, 612c, 612d, and 612e. Each peak of the transient 620 includes a corresponding decaying transient 610a, 610b, 610c, 610d, 610e, and 610f.

As in the embodiment of FIGS. 5A and 5B, the system obtains for FIGS. 6A and 6B (e.g., by sampling or measuring a current transient) a current output Ip from the biosensor due to application of the last electrical pulse (e.g., positive pulse 610) in the sequence 600 of electrical pulses 601, 602, 603, 604, 605, and 606. Alternatively, a series of output currents can be utilized instead of the current output. In particular, each of the output currents $I_{P2}$, $I_{P3}$, can be measured at respective time $T_{p2}$ and $T_{p3}$. Each of the time points $T_{p2}$ and $T_{p3}$ can be a time point which is about 75% of the total duration of the current transient starting at the peak and ending when the current becomes or by summation of the current outputs from $T_{p2}$ to $Tp_E$ (FIG. 6B) and $T_{p3}$ to $Tp_E$. The system also obtains a current output $I_N$ as an average or a summation of the output currents $I_{N1}$, $I_{N2}$, $I_{N3}$. As noted earlier, the system may determine the glucose concentration with the first and second current outputs $I_P$ and $I_N$ in any one of Equations 4, 5, 6, or combinations thereof. Alternatively, where the biosensor includes two working electrodes, the system may determine the glucose concentration with Equations 3 where each of the current $I_P$ and current $I_N$ can be obtained from each of the working electrodes. Specifically, an average of the current $I_P$ from each of the working electrodes can be used along with an average of the current $I_N$ from each of the working electrodes as the current I in Equation 3 above.

FIGS. 7A and 7B illustrate yet another embodiment in which the system obtains glucose concentration using a pulsed sequence of electrical signals. In the sequence of FIG. 7A, the interval "d" is longer than that of the duration or interval in FIG. 5A or FIG. 6A. In particular, the duration "d" is twice as long as the one in FIG. 5A or FIG. 6A, thereby extending the overall time at which the glucose reaction is measured from about 4 seconds to about 7 seconds.

Referring to FIG. 7A, the plurality of positive electrical pulses can include the first and next to the last pulse (e.g., 702 and 706) in the sequence of pulses. There is at least one negative electrical pulse (e.g., pulse 708) being the last pulse in the sequence of pulses. It is noted that the plurality of positive electrical pulses is applied over discrete spaced apart time-wise intervals "d" at which a voltage of the positive electrical pulse is held at a generally constant magnitude during each interval. At least one negative electrical pulse, for example, negative pulse 704 or 708 (FIG. 7A), is applied over at least one discrete time interval at which a voltage of the negative electrical pulse is held at a generally constant magnitude during each interval.

With reference to exemplary FIG. 7B, each of the pulses applied (in FIG. 7A) to the biosensor will cause the physical transformation involving the glucose and reagent to provide (in biosensor 100) an output transient 710 (in FIG. 7B) with corresponding peaks at the beginning of each output pulse (FIG. 7A). The peaks are delineated here as 712a, 712b, 712c, and 712d. The output transient 710 is represented here as current output over time and shown here as several transients 710a, 710b, 710c, and 710d in which each of the transients is decaying from the respective peaks 712a, 712b, 712c, and 712d. In particular, the system obtains (e.g., by sampling or measuring a current transient) a current output $I_P$ from the at least two electrodes of the biosensor due to application of an electrical pulse other than the first pulse in the sequence 700 of electrical pulses 702, 704, 706, and 708. In this case, the positive pulse that is utilized here must be other than the first positive pulse 702, which in this case is pulse 706. The current output $I_P$ can be measured at time Tp2 and represented by output current identifier $I_{P2}$ by summation of the output currents at each point of time from to $Tp_2$ to $T_{pE}$ (FIG. 7B). The system also obtains a current output $I_N$ from the biosensor due to application of the last electrical pulse (e.g., pulse 708) in the sequence of pulses 702, 704, 706, and 708. Because there are two negative pulses, the current output $I_N$ is taken as an average at time $T_{N1}$ and $T_{N2}$ or by summation of the output currents $I_{N1}$ and $I_{N2}$ (measured from $T_{N1}$ or $T_{N2}$ to respective $T_{nE}$). Thereafter, the system may determine the glucose concentration with the first and second current outputs $I_P$ and $I_N$ in any one of Equations 4, 5, 6, or combinations thereof. Where the system utilizes two or more working electrodes, the system may use the average of the two currents obtained from each of the working electrodes in any one of Equations 3-6, or combinations thereof.

Figure 8A:
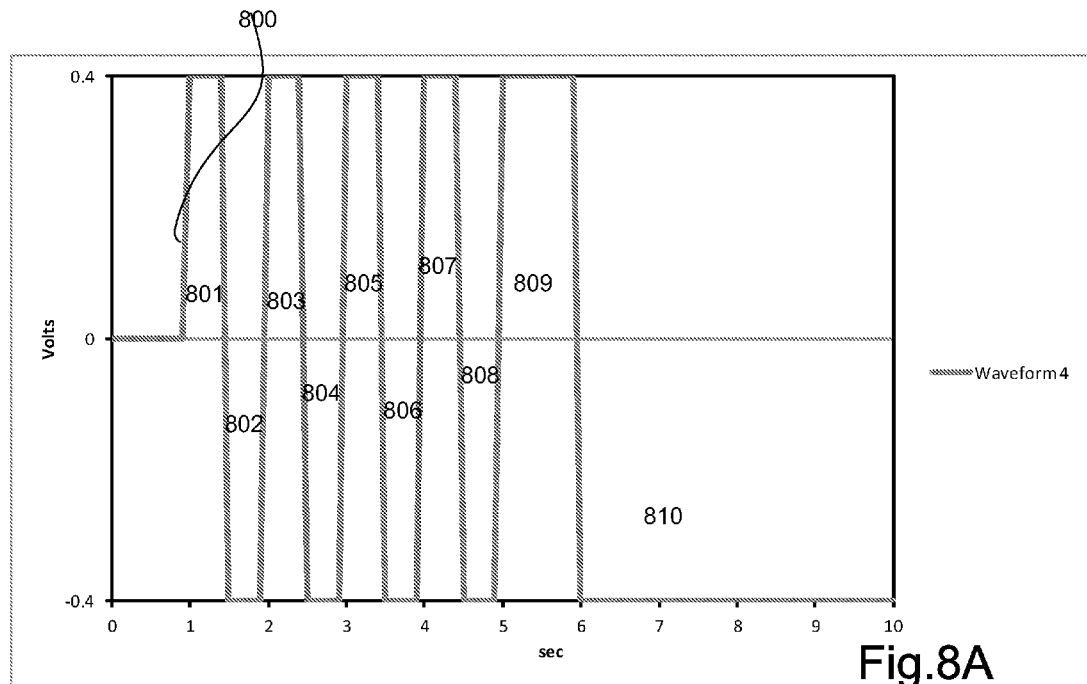
FIG. 8A illustrates a graph of ten electrical pulses being driven into the biosensor of the preferred embodiments.
Figure 8B:
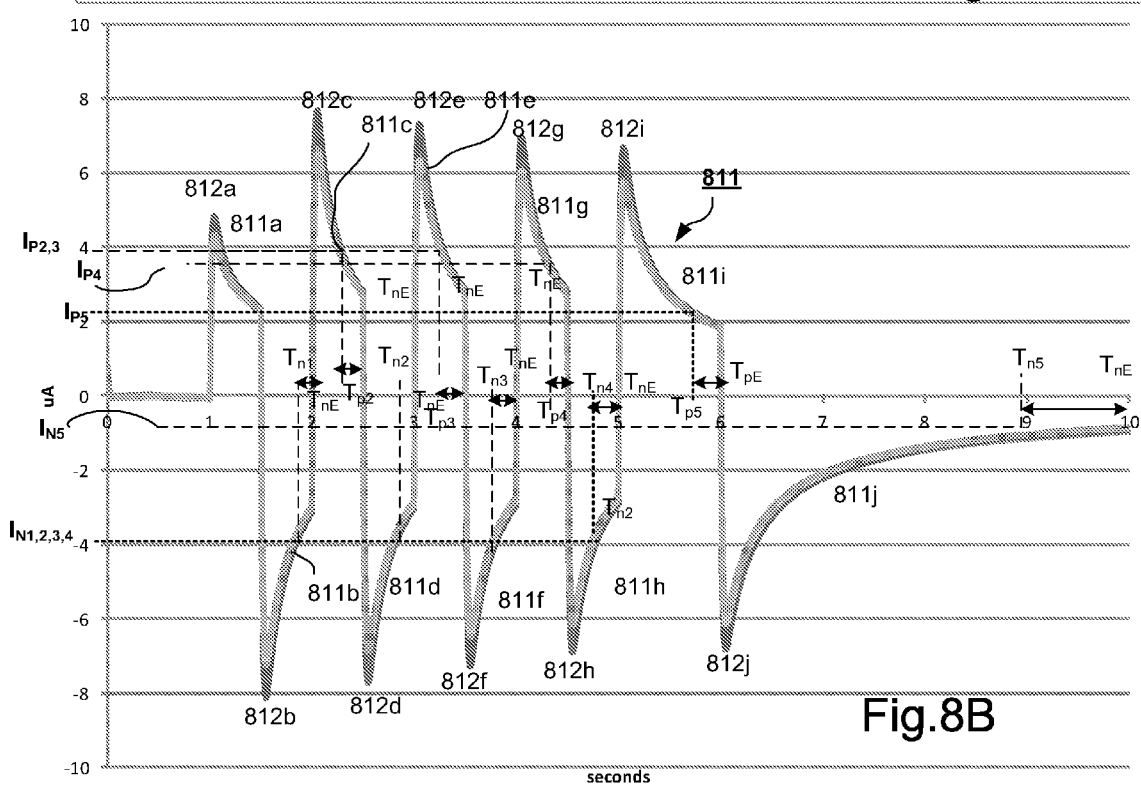
FIG. 8B illustrates a graph of ten corresponding output pulses from the biosensor that are due to the ten input pulses of FIG. 8A.
Figure 9C:
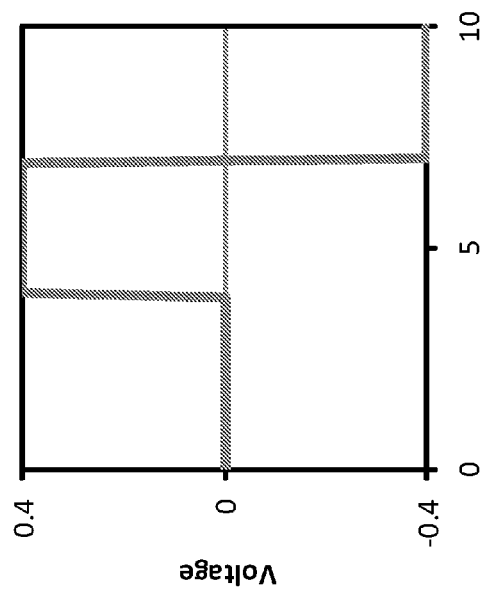
Figure 9D:
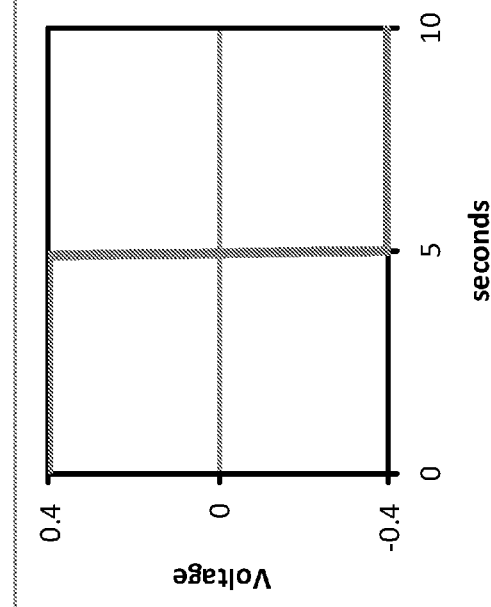

FIGS. 8A and 8B illustrate yet another embodiment in which the system obtains glucose concentration using a pulsed sequence of electrical potential 800. In this embodiment, the potential 800 is provided to the biosensor in the form of ten pulses (801-810) in which five of the pulses (801, 803, 805, 807, 809) are positive pulses and five of the pulses are negative (802, 804, 806, 808, 810). The duration of four positive pulses are generally equal to about 0.5 seconds whereas the duration of the last positive pulse 809 is about 1 second and the duration of the last negative pulse is about 4 seconds. The output from the biosensor is current transient 811 which includes peaks 812a, 812b, 812c, 812d, 812e, 812f, 812g, 812h, 812i and 812j with decaying current transients 811a, 811b, 811c, 811d, 811e, 811f, 811g, 811h, 811i, and 811j.

With reference to exemplary FIG. 8B, each of the pulses applied (in FIG. 8A) to the biosensor will cause the reaction in the biosensor 100 involving the glucose and reagent to provide an output transient 811a-811j (in FIG. 8B) with corresponding peaks 812a-812j at the beginning of each input pulse (FIG. 8A). The output transient 810 is represented here as current output over time and shown here as several transients 811a-811j in which each of the transients is decaying from the respective peaks 812a-812j. In particular, the system obtains (e.g., by sampling or measuring a current transient) a current output $I_P$ from the at least two electrodes of the biosensor due to application of the last electrical pulse (e.g., 706) in the sequence 800 of electrical pulses 808 and 809. As in previous embodiments described above, the system may obtain one or only one of the current outputs of the last positive pulse or the current output last negative pulse for determining the glucose concentration. The system may obtain an average of both the current output of the last positive pulse and the current output of the last negative pulse to determine the glucose concentration.

Alternatively, the system may obtain an average of output currents of all the pulses (positive and negative) except the first pulse to determine the glucose concentration. The output currents $I_{P2}$, $I_{P3}$, $I_{P4}$, $I_{P5}$ can be measured at respective time Tp2 ... $T_{p4}$ or by summation of the output currents at each predetermined time point Tp2 ... $T_{p4}$ (or duration) for each pulse (FIG. 8B). The system also obtains a current output $I_N$ from the biosensor due to application of a next to the last electrical pulse (e.g., pulse 808) in the sequence of pulses 801-810. The current output $I_N$ can be the current output of the last negative pulse 811j. Alternatively, current output $I_N$ can be represented as the average of output currents measured at time points $T_{N1}$ ... $T_{N5}$. The current output $I_N$ can also be represented by the average or a summation of the current outputs from $T_{N1}$ to $T_{NE}$, $T_{N2}$ to $T_{NE}$, $T_{N3}$ to $T_{NE}$, $T_{N4}$ to $T_{NE}$, and $T_{N5}$ to $T_{NE}$ (each time duration designated by a double-headed identifier). Thereafter, the system may determine the glucose concentration with the first and second current outputs $I_P$ and $I_N$ in any one of Equations 4, 5, 6, or combinations thereof. Where the system utilizes two or more working electrodes, the system may use the average of the two currents obtained from each of the working electrodes in any one of Equations 3-6, or combinations thereof.

In this system, the biosensor 100 may have a substrate on which the at least two electrodes are disposed with three electrodes, of which one of the three is a reference electrode and two of the three are working electrodes. The pulses can be any number of alternating pulses from 3 to about 10 and the magnitude of the positive electrical pulse can be from about 200 millivolts to about 600 millivolts and the magnitude of the negative electrical pulse can be from about −200 millivolts to about −600 millivolts, where the duration of the positive or negative electrical pulse can be any duration from about 0.25 seconds to about 2 seconds.

To obtain calibration curve for Waveforms 1-4 in order to assess the error or bias of the new technique compared to the known technique, current transients similar to those in FIGS. 5-8 were measured at a range of nominal blood glucose concentrations in the range 50 to 600 mg per dL. The current transients were interrogated as follows. In the case of the known constant voltage driving voltage of FIG. 4A, the average current between 4.81 and 5.00 second from the start of the glucose measurement was used to determine the glucose concentration whereas in the case of pulsed Waveforms 1-3 two current values were extracted. First, the average current measured during a predetermined time period within each time interval (e.g., the last and approximately 200 milliseconds of the final negative pulse) is obtained. Second, the average current measured during a predetermined time period within each time interval (e.g., the last and approximately 200 milliseconds of the final positive pulse). These current values were used together with reference measurements of glucose performed using a YSI 2700 clinical instrument (available from YSI LifeSciences at http://www.ysilifesciences.com/index.php?page=ysi-2700-select-bioprocess-monitoring), to give a baseline measurement of glucose against which the sensor-based measurements was compared to provide bias data and construct glucose calibration curves, which techniques are well known to those skilled in the art and for the sake of brevity, will not be described further.

At a nominal blood glucose concentration of about 70 mg/dL, the blood samples were spiked with interferent compounds, specifically acetaminophen, uric acid, ascorbic acid and dopamine (in FIGS. 10-13). The glucose values were measured in each interferent spiked solution. Comparable calibration curves were obtained using the final negative pulse of Waveform 1 and using the final positive and negative pulses for Waveforms 2, 3 and 4, glucose concentrations were calculated for each of the positive and negative pulses for Waveforms 1-4. Due to nonlinearity in the current versus reference glucose measurement relationship a quadratic calibration was employed in the case of all pulsed Waveforms.

Using the respective glucose calibration curves, the error or "bias" with respect to the reference glucose measurement was determined for each interferent compound. Bias measurements are presented in FIGS. 10A, and 10-12. Additionally, the effect of increasing interferent concentration (in this case uric acid) on the efficacy of the error current reduction (expressed in mg/dL glucose) was investigated, and the results are shown in FIG. 10B. The "bias" is an estimate of the relative error in the glucose measurement as compared to YSI referential datum, and can be determined with equations of the form:

$$\text{Bias}_{abs} = G_{calculated} - G_{reference} \qquad \text{Eq. 7}$$

for $G_{reference}$ less than 75 mg/dL glucose concentration.

The results presented in FIGS. 10A, 11-13, and 10B show that the error current due to the presence of irreversibly electrochemically active interferent compounds in the blood sample, and hence the measurement error (or "bias") in the glucose determination, is reduced in the case of the 'pulsed' Waveform (Waveforms 1-4) with respect to that in the case of a glucose determination made using the current response resulting from the application of a single, positive, voltage pulse (Waveform 0). Furthermore, the use of pulsed Waveform was effective in reducing the error current due to uric acid up to an added uric acid level of around 12 mg/dL, above which no further reduction was observed. This upper limit above which no further reduction was observed is above the range of uric acid concentrations typically encountered in human blood is in the range 3-9 mg/dL.

Figure 10A:
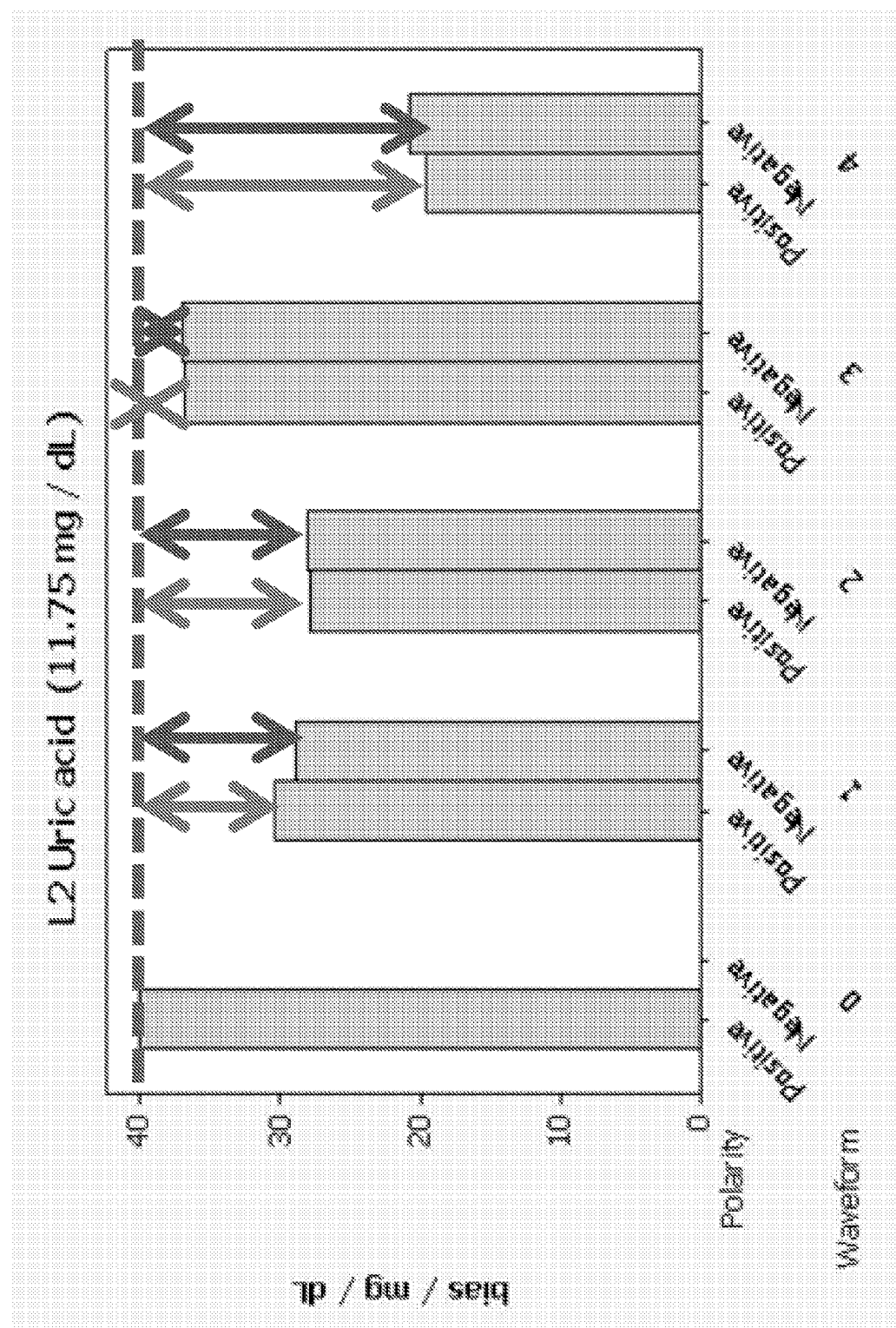
FIGS. 10A and 10B illustrate the reduction in bias when uric is added as an interferent to the measurement sample.
Figure 10B:
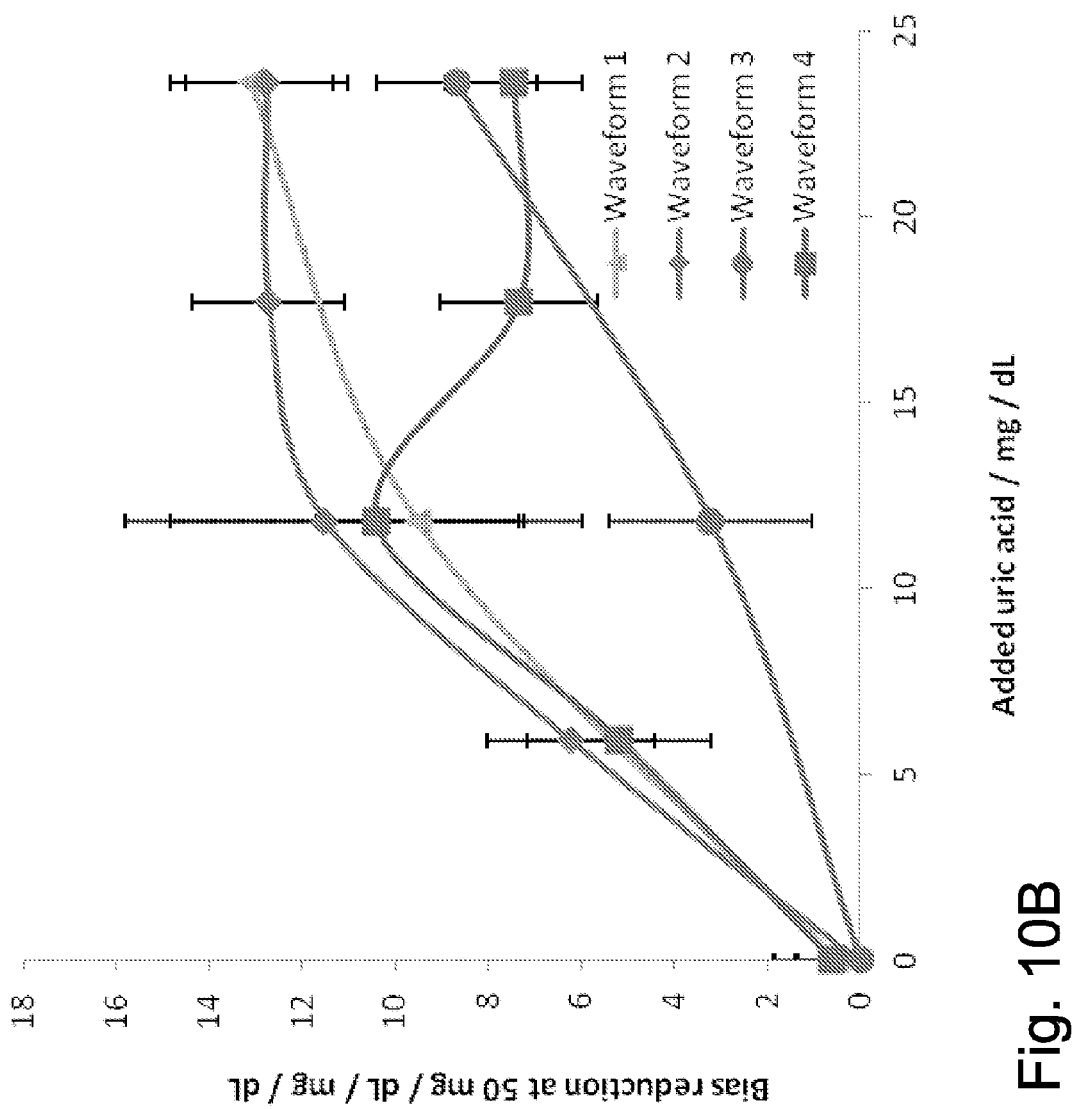

Referring to FIG. 10A, which is analyzed for bias due to uric acid, it can be seen that for the known Waveform "0", the bias is approximately 40 milligrams per deciliter ("mg/dL") whereas for the wave forms "1"; "2"; "3" and "4" (where each Waveform includes the positive last pulse and the next to last negative pulse), there is a reduction in the bias (delineated as arrows) that in percentage term, is considered by applicants to be advantageous. For example, in FIG. 10A, the largest percentage reduction in bias is about 50% for Waveform 4 and the lowest being approximately 10% for Waveform 3. Both Waveforms 1 and 2 in FIG. 10A are around 28% reduction in bias. Applicants further note that this reduction in bias improves linearly with respect to the amount of uric acid added to the glucose sample with a limit seeming to be reached at the concentration of about 15 mg of uric acid per deciliter, seen here in FIG. 10B.

This ability to reduce the bias by uric acid can be seen in a different format for each of the Waveforms 1-4 in FIG. 10B, as uric acid is added at 5.9 mg uric acid per deciliter (or 12.5 mg uric acid/dL) in the samples for Waveforms 1-4. For Waveform 1, the reduction in error or bias is approximately 6 mg/dL (or 12 mg/dL reduction in bias) for a virtual 1:1 correspondence. For Waveform 2, the improvements appear to be even greater than 1:1 when the amounts from approximately 5 mg/dL to 20 mg/dL of uric acid are added in the samples utilized in this waveform. Nevertheless, there appears to be a limit for both Waveforms 1 and 2 at which the reduction bias cannot be further improved with increasing amount of uric acid beyond approximately 15 mg of uric acid per deciliter. While Waveform 3 shows good bias reduction (approximately 3 mg/dL at uric acid concentration of 12 mg/dL and 8 mg/dL at uric acid concentration of 25 mg/dL) but not as good as Waveforms 1 and 2. Waveform 4 generally matches Waveforms 1 and 2 in bias reduction up to the uric acid concentration of 13 mg/dL. However, Waveform 4 is unable to match the performance of Waveforms 1 and 2 once the uric acid concentration increases beyond 13 mg/dL and only managed to almost match the bias reduction of Waveform 3.

For interferents (such as, for example, dopamine) that tend to cause the glucose concentration to read lower than referential YSI values, the reduction in the error (delineated here as arrows for each of the wave forms 1-4 in FIG. 11) is again substantial and unexpected by applicants in that almost all of the Waveforms reduced the bias due to dopamine by at least 70%. For example, in wave form 1, the glucose reading reads lower than referential YSI value by approximately 3 mg/dL whereas the known technique (wave form 0) obtains a glucose reading which is about 14 mg/dL lower than YSI for a 75% reduction in bias.

Figure 12:
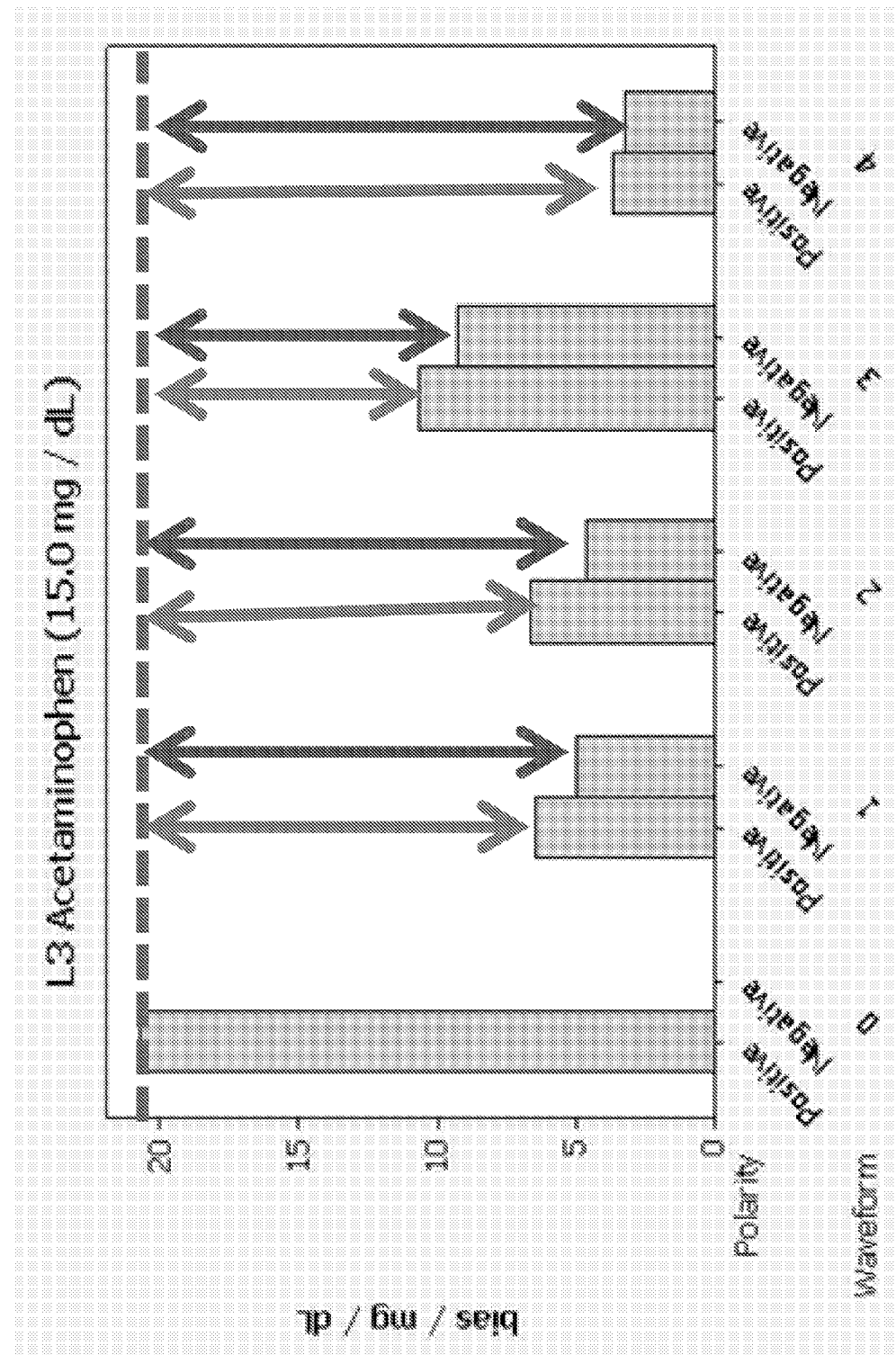
Figure 13:
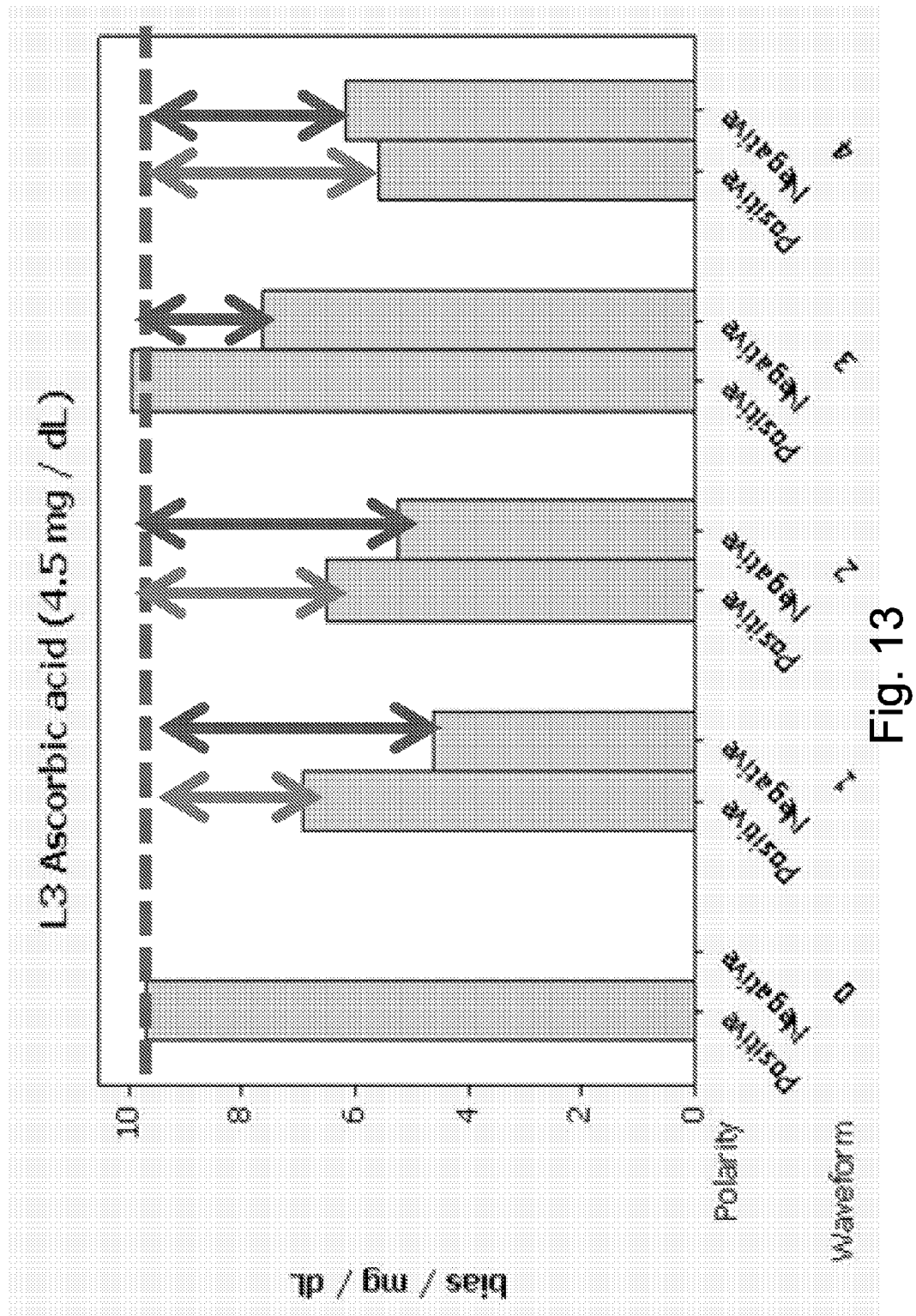

Other interferents were tested and the reduction in the glucose reading or bias in the glucose measurements as compared to referential YSI for these interferents were also substantial and unexpected. As shown in FIG. 12, for acetaminophen (at a concentration of 15 mg per deciliter), there is a reduction of at least about 20% in the bias of the glucose reading (as compared to referential) for Waveforms 1, 2, and 4. For acetaminophen as an interferent (at 15 mg per deciliter), the reduction in bias is very substantial at a maximum of about 75% (Waveform 4) and a minimum of about 50% (wave form 3). For ascorbic acid as an interferent (at 4.5 mg/dL), shown here in FIG. 13, the bias is reduced by at least 20% for Waveforms 1, 2 and 4.

Figure 14:
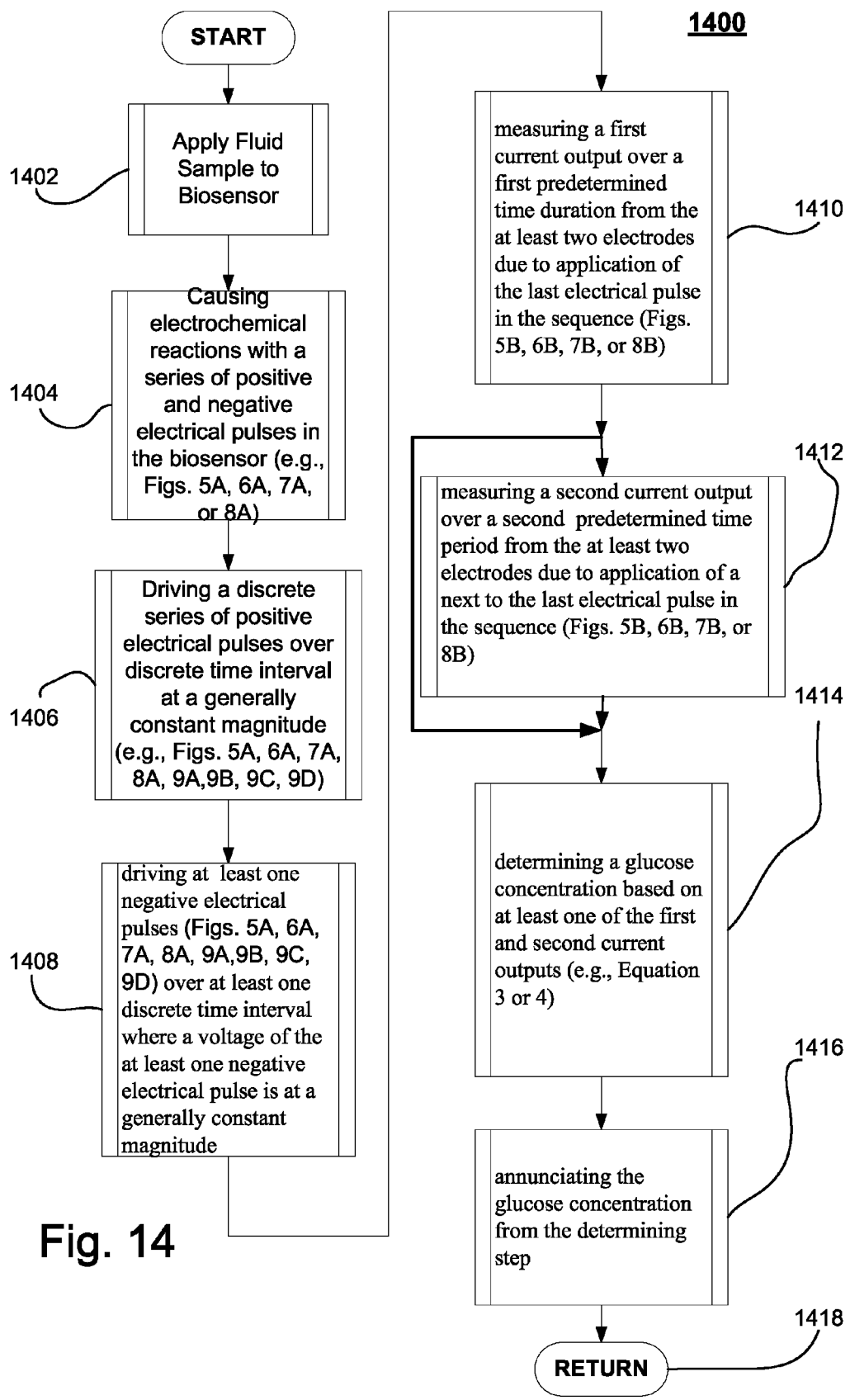
FIG. 14 illustrates a logic diagram for a method of determining a glucose concentration in accordance with the techniques described herein.

By virtue of the system described herein, a method to determine a glucose concentration can be achieved. An exemplary logic diagram is shown in FIG. 14. In this method, the steps may involve, at step 1402, depositing a physiological fluid sample on the reagent proximate the at least two electrodes of the biosensor. Typically, the biosensor is configured to allow for the fluid sample to react with the reagent of the biosensor. In particular, an initial poise delay is provided in the form of an open circuit. The purpose of this poise delay is to permit the sample to wet out the glucose sensing chemistry prior to the application of the initial voltage pulse (which may be of positive polarity), leading to the measurement of a peaked current response. In each of the exemplary Waveforms 1-4 a poise delay of about 1 second duration was applied. However, poise delays of, for example, about 0.5 second to about 5 seconds in duration may be appropriate, depending on the wetting rate of the glucose sensing chemistry. At step 1404, the method includes applying a plurality of positive and negative electrical pulses to the at least two electrodes in sequence with a plurality of positive electrical pulses with a positive electrical pulse being first in the sequence and at least one positive electrical pulse being next to the last pulse in the sequence. It is noted that in the preferred embodiments, an initial positive voltage pulse of duration of about 0.5 second to about 5 seconds is provided. The current response resulting from the application of this pulse is believed to contain an error current generated through the direct oxidation of interferent compounds in the blood. After the initial positive pulse, the system may switch to at least one negative voltage pulses of duration from about 0.5 to about 5 seconds. The current response resulting from the application of these pulses is believed to contain a reduced error current generated through the direct oxidation of interferent compounds in the blood. With subsequent positive and negative pulses (e.g., FIG. 5A, 6A, 7A, or 8A), it is believed that the current response (in e.g., FIG. 5B, 6B, 7B, or 8B) resulting from the application of these pulses contains a reduced error current generated through the direct oxidation of interferent compounds in the blood.

Referring back to FIG. 14, it is noted that the applying step 1404 further includes step 1406 of driving the plurality of positive electrical pulses over discrete time intervals and during each interval, a voltage of each of the positive electrical pulses is at a generally constant magnitude, and in step 1408 driving at least one negative electrical pulse over at least one discrete time interval and during the at least one discrete interval, a voltage of the at least one negative electrical pulse is at a generally constant magnitude, which is shown for illustrative purposes in FIGS. 5A, 6A, 7A, and 8A. The system can be configured to utilize only one of steps 1410 or 1412 or both steps 1410 and 1412 in its determination of the analyte. In the former configuration, the system can consider at step 1410, the system performs the step of measuring a first current output (FIGS. 5B, 6B, 7B, and 8B) from the biosensor over a first predetermined time duration from the biosensor due to application of at least one negative electrical pulse in the sequence. Alternatively, the system may consider only step 1412, in which the logic performs the step of measuring a second current output over a second predetermined time period from the biosensor due to application of at least one negative electrical pulse in the sequence. In the latter configuration, the system considers both steps 1410 and 1412 in order for the system to move to step 1414. At step 1414, the logic determines a glucose concentration based on at least one of the first and second current outputs; and annunciating the result (in step 1418) of the determining step 1416. In the determining step 1416, the glucose concentration can be determined by virtue of a suitable relationship representative of the proportion of actual glucose being transformed in the reaction with the reagent. Such suitable relationship may include Equation 3 or Equation 4. As used here, the term "annunciated" or "annunciating" and variations on the root term indicate that an announcement may be provided via text, audio, visual or a combination of all modes of communication to a user, a caretaker of the user, or a healthcare provider.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. An analyte measurement system comprising:
a biosensor having at least two electrodes with a reagent disposed proximate the at least two electrodes;
an analyte meter comprising:
a power supply;
memory for storage of data; and
a microprocessor coupled to the power supply and memory, and the biosensor, the microprocessor configured to determine an analyte concentration in a physiological sample by:
application of positive and negative electrical pulses to the at least two electrodes that repeat in sequence as a positive pulse, negative pulse, positive pulse and negative pulse, in which a voltage of at least one positive electrical pulse is at a generally constant magnitude during at least one discrete interval, followed by a voltage of at least one negative electrical pulse at a generally constant magnitude during at least one discrete interval;
obtain at least one current output over a predetermined time period from the at least two electrodes for each of the plurality of electrical pulses other than the first electrical pulse; and
calculate an analyte concentration based on the at least one current output.

2. An analyte measurement system comprising:
a biosensor having at least two electrodes with a reagent disposed proximate the at least two electrodes;
an analyte meter comprising:
a power supply;
memory for storage of data; and
a microprocessor coupled to the power supply and memory, and the biosensor, the microprocessor configured to determine an analyte concentration in a physiological sample by:
application of positive and negative electrical pulses to the at least two electrodes that repeat in sequence as a positive pulse, negative pulse, positive pulse and negative pulse, in which the sequence of electrical pulses is applied over discrete intervals and during each interval, a voltage of each of the positive electrical pulses is at a generally constant magnitude, and a voltage of at least one negative electrical pulse at a generally constant magnitude;
obtain at least a first current output from the from the at least two electrodes for each of a first predetermined time period due to application of at least one positive electrical pulse in the sequence other than the first electrical pulse;
obtain at least a second current output from the at least two electrodes for each of a second predetermined time period due to application of at least one negative electrical pulse in the sequence; and
calculate an analyte concentration based on at least one of the first and second current outputs.

3. The system of claim 1, in which the biosensor comprises a substrate on which the at least two electrodes are disposed, wherein the at least two electrodes comprise three electrodes, of which one of the three includes a reference electrode and two of the three are working electrodes.

4. The system of claim 1, in which the at least one current output comprises a negative current output of the last electrical pulse.

5. The system of claim 4, in which the microprocessor is configured to calculate the analyte concentration with an equation of the form:

$$G_N = \frac{(|I_N| - \text{Intercept})}{\text{Slope}}$$

where
$I_N$ comprises a negative current output from the last electrical pulse of the sequence;
Slope comprises the value obtained from calibration testing of a batch of biosensors of which this particular biosensor comes from; and
Intercept comprises the value obtained from calibration testing of a batch of biosensors of which this particular biosensor comes from.

6. The system of claim 2, in which the microprocessor is configured to calculate the analyte concentration with an equation of the form:

$$G = \frac{(|I_E| - \text{Intercept})}{\text{Slope}}$$

where
$I_E$ comprises an average of the first current output $I_P$ and second current output $I_N$;
$I_P$ comprises at least one current output or an average current output of the first output currents measured from each positive pulse other than the first positive pulse;
$I_N$ comprises at least one current output or an average current output of the second output currents measured from each negative pulse in the sequence;
Slope comprises the value obtained from calibration testing of a batch of biosensors of which this particular biosensor comes from; and Intercept comprises the value obtained from calibration testing of a batch of biosensors of which this particular biosensor comes from.

7. The system of claim 6, in which the sequence comprises a number of k pulses and each of the first output currents and second output currents comprises an output current measured at a predetermined time within each of the k number of pulses.

8. The system of claim 7, in which each of the first output currents comprises a summation of the positive output currents over a predetermined time duration during each pulse in the sequence of k pulses.

9. The system of claim 7, in which each of the second output currents a summation of the negative output currents over a predetermined time duration during each pulse in the sequence of k pulses.

10. The system of claim 9, in which the number k is at least 2.

11. The system of claim 5, in which the microprocessor is configured to calculate the analyte concentration with an equation of the form:

$$G_P = \frac{(|I_P| - \text{Intercept})}{\text{Slope}}$$

where
$I_P$ comprises an average of output currents measured from positive electrical pulses of the sequence other than the first positive electrical pulse in the sequence;
Slope comprises the value obtained from calibration testing of a batch of biosensors of which this particular biosensor comes from; and
Intercept comprises the value obtained from calibration testing of a batch of biosensors of which this particular biosensor comes from.

12. The system of claim 11, in which the analyte concentration comprises an average of the sum of the analyte concentrations $G_p$ and $G_N$.

13. The system of claim 3, in which the sequence of pulses comprises a k number of pulses and the first current comprises an average of current outputs over the first predetermined time period within each pulse of the sequence of k pulses.

14. The system of claim 3, in which the sequence of pulses comprises a k number of pulses, and the first current comprises a summation of current outputs over the first predetermined time period within each pulse of the sequence of k pulses in which k comprises any whole number of at least 2.

15. The system of claim 3, in which the sequence of pulses comprises a k number of pulses, and the second current comprises an average of current outputs over the second predetermined time period within each pulse of the sequence of k pulses in which k comprises any whole number of at least 2.

16. The system of claim 3, in which the sequence of pulses comprises a k number of pulses, and the second current comprises a summation of current outputs over the second predetermined time period within each pulse of the sequence of k pulses in which k comprises any whole number of at least 2.

17. The system of claim 3, in which each of the first and second predetermined time periods comprises about the same duration of time.

18. The system of claim 3, in which the first predetermined time period comprises about 200 milliseconds and the second predetermined time period comprises about 200 milliseconds.

19. The system of claim 3, in which the magnitude of the positive electrical pulse comprises about 400 millivolts and the magnitude of the negative electrical pulse comprises about negative 400 millivolts.

20. The system of claim 3, in which the duration of the positive electrical pulse comprises about any duration from about 0.5 seconds to about 5 seconds.

21. The system of claim 3, in which the duration of the negative electrical pulse comprises about any duration from about 0.5 seconds to about 5 seconds.

22. A method to determine analyte concentration in a physiological sample with analyte meter having a microprocessor coupled to a power supply and memory and a biosensor having a reagent disposed on at least two electrodes, the method comprising:

depositing a physiological fluid sample on the reagent proximate the at least two electrodes of the biosensor;

applying a plurality of positive and negative electrical pulses to the at least two electrodes that repeat in sequence as a positive pulse, negative pulse, positive pulse and negative pulse with a positive electrical pulse being first in the sequence and at least one positive electrical pulse being next to the last pulse in the sequence, the applying step includes:

driving the plurality of positive electrical pulses of the sequence over discrete time intervals and during each interval, a voltage of each of the positive electrical pulses is at a generally constant magnitude, and driving a plurality of negative electrical pulses of the sequence over at least one discrete time interval and during the at least one discrete interval, a voltage of the at least one negative electrical pulse is at a generally constant magnitude;

measuring a first current output over a first predetermined time duration from the at least two electrodes due to application of at least one positive electrical pulse in the sequence other than the first positive electrical pulse;

measuring a second current output over a second predetermined time period from the at least two electrodes due to application of at least one negative electrical pulse in the sequence;

determining a analyte concentration based on at least one of the first and second current outputs; and annunciating the analyte concentration from the determining step.

23. The method of claim 22, in which the determining step comprises calculation of the analyte concentration with an equation of the form:

$$G = \frac{(|I_E| - \text{Intercept})}{\text{Slope}}$$

and where:
$I_E$ comprises an average of the first current output $I_P$ and second current output $I_N$;
$I_P$ comprises an average current output of the first output currents measured from each positive pulse other than the first positive pulse;
$I_N$ comprises an average current output of the second output currents measured from each negative pulse in the sequence;

Slope comprises the value obtained from calibration testing of a batch of biosensors of which this particular biosensor comes from; and Intercept comprises the value obtained from calibration testing of a batch of biosensors of which this particular biosensor comes from.

* * * * *